(12) United States Patent
Taylor

(10) Patent No.: US 8,702,236 B2
(45) Date of Patent: Apr. 22, 2014

(54) BINOCULAR PUPILLOMETERS

(75) Inventor: Daniel Robert Stafford Taylor, Christchurch (GB)

(73) Assignee: Procyon Instruments Limited, London (GB)

( * ) Notice: Subject to any disclaimer, the term of this patent is extended or adjusted under 35 U.S.C. 154(b) by 277 days.

(21) Appl. No.: 12/736,050

(22) PCT Filed: Mar. 4, 2009

(86) PCT No.: PCT/GB2009/000595
§ 371 (c)(1),
(2), (4) Date: Mar. 21, 2011

(87) PCT Pub. No.: WO2009/109750
PCT Pub. Date: Sep. 11, 2009

(65) Prior Publication Data
US 2011/0170064 A1 Jul. 14, 2011

(30) Foreign Application Priority Data

Mar. 4, 2008 (GB) .................................. 0804090.9
Dec. 31, 2008 (GB) .................................. 0823699.4

(51) Int. Cl.
*A61B 3/14* (2006.01)
*A61B 3/00* (2006.01)
*A61B 3/113* (2006.01)

(52) U.S. Cl.
CPC ...................................... *A61B 3/113* (2013.01)
USPC .......................................... 351/209; 351/246

(58) Field of Classification Search
USPC ................................................ 351/209, 246
See application file for complete search history.

(56) References Cited

U.S. PATENT DOCUMENTS

| 5,617,872 | A | 4/1997 | Scinto et al. |
| 5,704,369 | A | 1/1998 | Scinto et al. |
| 6,022,109 | A | 2/2000 | Dal Santo |
| 6,116,736 | A | 9/2000 | Stark et al. |
| 2002/0024633 | A1 | 2/2002 | Kim et al. |

FOREIGN PATENT DOCUMENTS

| WO | WO2004/016153 | 2/2004 |
| WO | WO2006/032920 | 3/2006 |

OTHER PUBLICATIONS

C.M. Privitera, et al., "A binocular pupil model for simulation of relative afferent pupil defects and the swinging flashlite test" Biological Cybernetics, vol. 94, No. 3, p. 215-224, Mar. 1, 2006.
Great Britan Search Report for GB0903801.9 of Apr. 16, 2009.
H.J. Wyatt, et al., "Pupillary light reflex in humans Evidence for an unbalanced pathway from nasal retina, and for signal cancellation in bainstem" Vision Research, vol. 21, No. 4, p. 513-525, Jan. 1, 1981.
International Search Report for PCT/GB2009/000595 of Jun. 3, 2009.

(Continued)

*Primary Examiner* — Jack Dinh
(74) *Attorney, Agent, or Firm* — Hueschen and Sage

(57) ABSTRACT

A binocular pupillometer apparatus is provided with processing means to calculate the relative afferent pupillary defect (RAPD) in a subject. The RAPD is calculated as the shift required to bring the two pupillary responses of the left and right eyes into coincidence. Where the responses are not parallel, modified pupillary responses are determined having the same area difference between the responses and an average rate of change with respect to stimulation intensity. The RAPD is calculated from the modified pupillary responses rather than the observed responses. Improvements to the pupillometer include a divider positioned between the left and right stimulating channels.

9 Claims, 12 Drawing Sheets

(56) References Cited

OTHER PUBLICATIONS

Privitera, et al., "a binocular pupil model for simulation of relative afferent pupil defect RAPD" Proceedings of the 26th Annual International Conference of the IEEE Engineering in Medicine and Biology Society, vol. 3, p. 711-714, Sep. 1, 2004.

Written Opinion of the International Searching Authority for PCT/GB2009/000595.

Dictionary of Physics, Longman Group Ltd., Great Britain, 1977, pp. 38-39.

Amplitude (mm)

Stimulus Intensity (dB)

1.8mm L 1.5mm R

Amplitude (mm)

Intensity (dB)

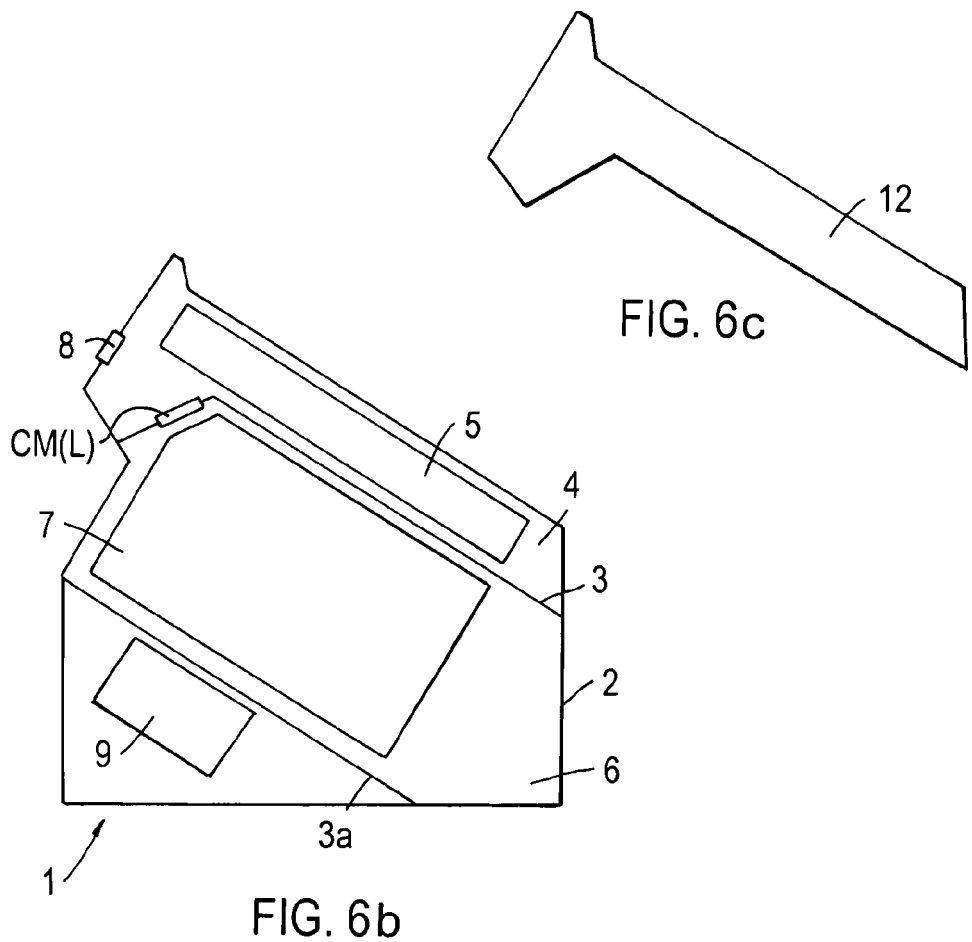
FIG. 6c
FIG. 6b
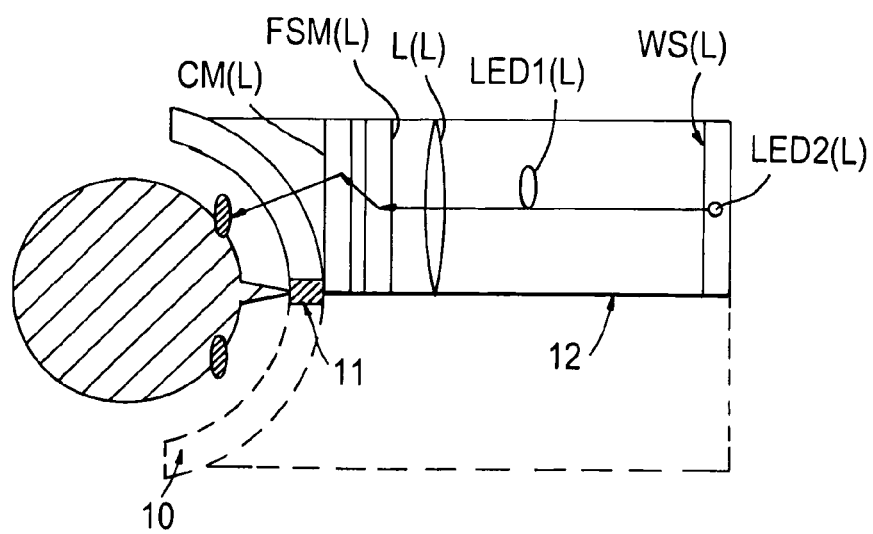
FIG. 7

BINOCULAR PUPILLOMETERS

This invention relates to binocular pupillometers, i.e. to apparatus for determining pupil dimensions in respect of the eyes of a subject, generally (although not necessarily exclusively) a human subject. In one embodiment the invention concerns a binocular pupillometer for assessing relative afferent pupillary defect (RAPD) in a subject. It also relates to the use of such pupillometers.

Pupillometers have many different uses. One is the assessment of relative afferent pupillary defect, a condition wherein nerve signals from the eye to the brain are unilaterally compromised, for example by retinal lesions or by damage to the optic nerve. In general, the right and left pupils react bilaterally to a light stimulus, so that when such a stimulus is applied to one eye only, both pupils will contract. In healthy subjects the amounts of pupillary contraction will be the same whichever eye is stimulated; where relative afferent pupillary defect is present, however, both pupils will contract in response to a unilateral stimulus, but this bilateral contraction is smaller when the stimulus is applied to the affected eye.

The traditional clinical procedure for diagnosis of relative afferent pupillary defect is the swinging flashlight test. This employs a small handheld flashlight which is shone into each eye alternately for one or two seconds, the clinician judging whether there is any inequality in the magnitude of the pupillary reactions. A set of small neutral density filters may then be used to estimate the magnitude of any observed defect, the flashlight being occluded with such a filter when shone into the healthy eye. The density of the filter is adjusted until filtered illumination of the healthy eye and unfiltered illumination of the affected eye produce equal pupillary responses, this density providing an index of the magnitude of the afferent pupillary defect.

Whilst quick and simple, this procedure is inevitably subjective and therefore liable to intraoperative variation. Moreover, since the procedure requires attenuation of stimulus to the eye with the larger response, the final measurement will necessarily be made at a relatively low response level, resulting in a loss of resolution and an escalation of measurement errors.

Kalaboukhova et al., *Neuro-Ophthalmology* 30, pp. 7-15 (2006), describe an objective method for measuring relative afferent pupillary defect using a custom-built pupillometer consisting of two digital high-resolution video cameras for detection of pupillary response (one for each eye), two white light-emitting diode lamps allowing alternating stimulating illumination of the eyes, and a background infrared illumination device. Two pasteboard screens fitting on each side of the nose separate the eyes and prevent stray light entering an eye from the contralateral side. The apparatus is set up in a darkroom and the subject is required to look at a distant dark red fixation light at the other end of the room in order to avoid accommodative miosis. Alternating light stimulation of a 0.5 second pulse followed by a 1 second pause was found to be the best stimulus pattern for relative afferent pupillary defect detection, and it was reported that this form of pupillometry could distinguish eyes with glaucoma from normal eyes with good sensitivity and specificity.

It will be appreciated that the substantial apparatus requirements, including the necessary electronic circuitry as well as the need to provide a dedicated darkroom, limit the applicability of this procedure and render it considerably expensive.

Portable binocular pupillometers in which the stimulating means and the means for detecting pupillary response are commonly housed to form an integrated unit are known in the art, for example as described in WO-A-94/07406 and WO-A-2006/032920. The latter document also describes a pupillometric procedure for diagnosis of relative afferent pupillary defect in which light stimulus pulses are alternately presented to each eye at four or more intensity levels, with each stimulus level optionally being repeated one or more times. One or more pupillary response parameters, such as depth of constriction (e.g. as measured by change in pupil diameter or area), maximum or average speed of constriction, latency period between onset of stimulus and onset of constriction, redilation time or time to reach a specific degree (e.g. 25%, 50% or 75%) of constriction and/or redilation are recorded, and the average values of the chosen parameter(s) for each stimulation level are then plotted (e.g. graphically or digitally) against the level intensities to give a pupillary response profile.

In this procedure the response profiles for the eyes of healthy subjects will substantially completely overlap. For subjects with relative afferent pupillary defect, on the other hand, stimulation of one eye will generate a consistently lower response than does stimulation of the other eye. The extent of the disorder may be quantified by determining the shift between the two profiles along the direction of the stimulus intensity axis, since this represents the light intensity scaling factor required to bring the two profiles into coincidence, and so is an equivalent of the neutral filter density magnitude obtained in the swinging flashlight test.

After careful investigation, the present inventor has discovered that in some cases, for example in unilaterally diseased patients, or bilaterally diseased in which the damage is asymmetrical, unilaterally diseased patient, or bilaterally diseased in which the damage is asymmetrical (e.g., in early glaucoma), the stimulation of one eye produces a lower amplitude response than the other, and consequently the amplitude response lines are not parallel, i.e. the rate of change of pupillary response with stimulation intensity for each eye is different. If the technique taught in WO 2006/032920 is applied to the observed pupillary responses of such patients, it can give rise to misleading results.

In order to solve this problem, according to a first broad aspect, the present invention provides a new algorithm for calculating RAPD which is executed automatically on processing means. The algorithm includes the steps of:

determining an apparent pupillary response for each of the left and right eyes with respect to intensity from recorded pupillary response data, wherein the apparent pupillary responses of the left and right eyes are not parallel to each other;

generating modified pupillary response data where the rate of change of pupillary response with stimulation intensity is intermediate the apparent pupillary responses of the left and right eyes;

calculating a value for relative afferent pupillary defect based on the modified pupillary response data; and outputting said value for relative afferent pupillary defect which is based on the modified pupillary response data.

Viewed from another aspect, the present invention provides a binocular pupillometer apparatus for assessing relative afferent pupillary defect in a subject means comprising: a binocular pupillometer comprising stimulating means arranged to apply a plurality of stimulating visible light pulses of different intensities independently to each eye and sensing means arranged to generate and record separate pupillary response data in respect of the left and right eyes, the apparatus further including processing means arranged to calculate relative afferent pupillary defect of a subject by:

(i) determining an apparent pupillary response for each of the left and right eyes with respect to intensity from the recorded pupillary response data, wherein the apparent pupillary responses of the left and right eyes are not parallel to each other;

(ii) calculating an area difference D between the apparent pupillary responses of the left and right eyes with respect to intensity;

(iii) generating modified pupillary responses for the left and right eyes which are parallel to each other, have a gradient which is intermediate the apparent pupillary responses of the left and right eyes and are separated by the area difference D;

(iv) calculating a value for relative afferent pupillary defect based on the modified pupillary responses of the left and right eyes; and (v) outputting said value for relative afferent pupillary defect which is based on the modified pupillary responses.

Preferably the processing means is a processor located within a housing of the binocular pupillometer. A screen may be provided on the housing to display the outputted value. In an alternative arrangement it may be a processor of a computer which is in communication with the binocular pupillometer, for example, via an electrical lead such as a USB cable, a connectionless coupling such as infra red, WiFi or Bluetooth communication, or through communication to a computer via the internet.

The binocular pupillometer is preferably an integrated binocular pupillometer comprising eyepieces for positioning against the eyes of the subject, sensing means adapted to generate and record separate pupillary response data in respect of the left and right eyes, and, commonly housed therewith, left and right stimulating means adapted to apply stimulating visible light pulses independently to said eyes in turn, wherein the left and right stimulating means are optically separated by dividing means and each comprise an illuminable screen which has a visible fixation point associated therewith and which is viewable through an object lens positioned between said screen and said eyepiece, said screen and lens being configured such that the observable field of view is at least 9°. The pupillometer is preferably programmed to generate a sequence of pulses of visible light for each eye, the pulses being delivered independently to each eye in turn, as a rapid series of flashes, the flashes being symmetrically interleaved between the left and right channels and being supplied as a set of flashes at one of three or more different intensity levels. This enables the pupillary responses for both the left and right eyes to be measured under essentially the same conditions at a given point in time without disturbing the arrangement of the subject to the pupillometer.

While this is a preferred form of binocular pupillometer, it is envisaged that the algorithm on the processing means has much wider application and so can be used with other forms of pupillometer that measure RAPD by applying pulses of visible light to each eye independently at a number of different intensities and recording the resulting pupillary response of each eye, and the data collected from such devices.

The apparent pupillary responses are calculated as straight line fits of the response data, for example, of the form $y=mx+c$, where y is the recorded amplitude in mm, x is the intensity of the illumination from the retina in dB, m is the gradient of the straight line response and c is the intercept on the amplitude axis. The gradient of the modified pupillary responses is intermediate that of the apparent pupillary responses, in the sense that it is somewhere between that of the left and right apparent responses. In the case where the response of the right eye is steeper than that of the left, the gradients for the left eye ($m_l$), modified ($m_m$) and right eye ($m_r$) responses would satisfy the function $m_l < m_m < m_r$, and vice versa if the opposite condition applied. Ideally the gradient of the modified responses is within 25% of the halfway position between the two apparent pupillary responses, more preferably within 10%. Most preferably, the modified response is an average of the apparent left and right eye pupillary responses. It is also envisaged that in other embodiments the modified pupillary responses may be the mode, median or some other function of the apparent left and right pupillary responses which sets the slope of the modified pupillary responses at approximately the midway gradient.

Preferably the area difference D between the apparent pupillary responses is calculated by integrating the amplitude of each of the apparent pupillary responses with respect to intensity and subtracting one from the other. Preferably the area difference D is calculated over an intensity range of 20 dB, which corresponds to a hundred fold change in lux.

The modified left and right eye pupillary responses are preferably straight line responses, and define the upper and lower sides of a parallelogram. The other sides of the parallelogram may be provided by the limits on the intensity axis, for example, 0 dB and 20 dB.

In an alternative embodiment, the processing means generates an intermediary pupillary response, which is substantially midway between the apparent pupillary responses, for example, an average of the two, and from this, either one or both of the modified pupillary responses for the left and right eyes is determined by taking into account the area difference D between the apparent pupillary responses (D/2 where just one modified pupillary response is determined).

The RAPD can be calculated by determining the shift along the intensity axis that is required to bring the two modified pupillary responses into coincidence, or it can be calculated by determining the shift along the intensity axis that is required to bring the intermediary and one modified pupillary response into coincidence and then doubling that amount. The shift, and hence the value for the RAPD, may be calculated by determining the separation of the responses at a given amplitude. Preferably the separation is calculated for the amplitude where the lower modified pupillary response intercepts the intensity axis (the y-axis) at a value of 0 dB.

Preferably the processing means of the binocular pupillometer apparatus calculates and outputs a value for RAPD based on apparent pupillary responses which are measured for each eye under direct stimulation conditions. Preferably the processing means of the binocular pupillometer apparatus also calculates and outputs a value for RAPD based on apparent pupillary responses which are measured for each eye under consensual stimulation conditions.

The algorithm for determining RAPD in accordance with this new area normalisation method may also have application in other forms of binocular pupillometer, and accordingly, from another aspect the invention also provides a method of assessing relative afferent pupillary defect in a subject comprising:

(i) determining an apparent pupillary response for each of left and right eyes with respect to intensity from recorded pupillary response data, wherein the apparent pupillary responses of the left and right eyes are not parallel to each other;

(ii) calculating an area difference D between the apparent pupillary responses of the left and right eyes with respect to intensity;

(iii) generating modified pupillary responses for the left and right eyes which are parallel to each other, have a gradient which is intermediate the apparent pupillary responses of the left and right eyes and are separated by the area difference D;

(iv) calculating a value for relative afferent pupillary defect based on the modified pupillary responses of the left and right eyes; and (v) outputting said value for relative afferent pupillary defect which is based on the modified pupillary responses.

In an alternative, the present invention provides a method of assessing relative afferent pupillary defect in a subject comprising, in place of step (iii), a step of calculating an intermediary pupillary response with respect to intensity which is intermediate the apparent pupillary responses of the left and right eyes and determining a modified pupillary response for the left or right eye with respect to intensity which follows the intermediary pupillary response, before the steps of calculating a value for relative afferent pupillary defect based on the intermediary pupillary response and modified pupillary response of the left or right eye, and outputting said value for relative afferent pupillary defect which is based on the intermediary and modified pupillary responses. Preferably the step of outputting the value for relative afferent pupillary defect (RAPD) includes outputting a value for RAPD based on apparent pupillary responses which are measured for each eye under direct stimulation conditions and outputting a value for RAPD based on apparent pupillary-responses which are measured for each eye under consensual stimulation conditions. The other preferred features described above in relation to the apparatus apply equally to this embodiment.

The method may be embodied within software provided on a computer program product or developed into the hardware of a binocular pupillometer.

WO-A-2006/032920 describes an integrated binocular pupillometer that has been recognised as a powerful clinical tool. While substantial progress has been made in binocular pupillometry, it would be desirable to make further advances which result in improvements in accuracy and precision of measurements.

According to a further aspect of the invention there is provided an integrated binocular pupillometer for assessing relative afferent pupillary defect in a subject and comprising eyepieces for positioning against the eyes of said subject, sensing means adapted to generate and record separate pupillary response data in respect of the left and right eyes, and, commonly housed therewith, left and right stimulating means adapted to apply stimulating visible light pulses independently to said eyes in turn, characterised in that said left and right stimulating means are optically separated by dividing means and each comprise an illuminable screen which has a visible fixation point associated therewith and which is viewable through an object lens positioned between said screen and said eyepiece, said screen and lens being configured such that the observable field of view is at least 9°, preferably 14°, more preferably 20° or more.

An important change in the binocular pupillometer since WO-A-2006/032920 has been to ensure perfect isolation between the left and right stimulus channels. The inventor has found that due to the highly logarithmic response of the pupil to changes in light intensity, if the right eye receives as little as 1% of the light intended for the left eye, it responds with a significant constriction. This directly affects the apparent RAPD, i.e., the RAPD which is observed in the subject using the technique taught, for example, in WO-A-2006/032920. Thus even the dim light of a common visual fixation point has been found to be enough to affect the apparent RAPD. By reducing the cross-contamination to less than 1%, for example, by providing each channel with its own visual fixation point and by optically separating the left and right stimulating means with a dividing means, the sensitivity and accuracy of the measured pupillary response and the RAPD is thereby significantly improved. In practice, it has been found that it is possible to reduce the cross-contamination to substantially less than 1%, for example, to less than 0.1%, and in most cases even less than 0.01%. Essentially there should be no detectable cross-contamination of light between the stimulus channels when using a lux meter positioned at an eyepiece of the device.

The binocular pupillometer of WO-A-2006/032920 has a housing comprising two moulded shells forming the outer left and right sides of the pupillometer, the shells together including an internal partition to define a first pocket for containing the visible optics of the left and right stimulating means and a second pocket for containing the infra red optics of the sensing means. The partition also serves to hold a cold mirror which allows infra red light to pass from the first pocket into the second pocket while keeping the visible light within the first pocket. In the present invention, the binocular pupillometer may be characterised in that a dividing means is provided between the left and right channels of the stimulating means to optically separate them. This has required the provision of two visible fixation points, one for each of the left and right illuminable screens.

Thus preferably the dividing means comprises a physical barrier within the housing, for example, a septum. The dividing means may be a separate component, for example, a planar element which has been cut with an outline that follows the internal profile of the housing where the left and right shells of the housing meet. For the most part, the dividing means may comprise any material which is able to isolate the stimulus channels, such as a cardboard divider, a plastic web or wall of the housing, or other physical barrier acting as a septum within the housing. Preferably the dividing means is in the form of a barrier that extends from the illuminable screens, preferably from behind the illuminable screens, all the way along the optics that provide the pupil stimulus right up to the eyepieces, in other words the barrier preferably extends the length of the left and right optical trains that are used to stimulate the eyes. Such an arrangement of shells and a central dividing means is advantageous from the point of view of manufacturing the binocular pupillometer, allowing the components to be fitted easily and precisely before the shells are connected together.

In one preferred embodiment the dividing means is extended all the way to the nose of the patient by incorporating a resilient member which extends beyond the housing, for example in the form of a foam divider. This has been found to provide excellent isolation between the left and right stimulus channels.

Preferably the isolation is improved further by providing a resilient seal, for example, an oval shaped seal enclosing both eyepieces, and a resilient member to contact a central region of the patient's face. In one embodiment, the resilient member is in the form of a cushion, preferably of light impermeable foam, which extends from the housing of the binocular pupillometer to contact the bridge of the patient's nose. Preferably the foam is a dark coloured foam, for example, grey or black foam. In another embodiment, the resilient member may be of a compliant plastic, rubber or other similar material which moulds to the shape of the patient's face to isolate the channels. In another arrangement, individual cups of a compliant material may be provided on the eyepieces to seal around the eye of the patient to prevent light escaping.

Preferably the optical trains for stimulating and observing the left and right eyes respectively are distinct, in the sense that duplicate mirror systems are provided for the left and right channels. In the arrangement of WO-A-2006/032920, the cold mirrors and face surface mirrors were single pieces that were used to view the left and right optical stimuli. In contrast, the cold and face-surface mirrors within the stimulating optics of the embodiments of the present invention are preferably split into two halves separated by the dividing means.

Thus, just a few minor changes to the known apparatus have been found, unexpectedly, to result in significant improvements in the accuracy and precision of the measurements taken using these binocular pupillometers. The increased resolution and clinical reliability of the measurements that results from this means that the binocular pupillometers of the present invention offer a new powerful clinical tool that can be used reliably in a number of applications.

For example the use of binocular pupillometers has been suggested in the past for the detection of glaucoma. Glaucoma is one of the most likely causes of RAPD. Various structural and functional tests are already well established for the detection of glaucoma such as measuring eye pressure (tonometry) and visual field (perimetry), all of which have advantages and disadvantages. However a common problem with these established tests is that they offer low precision and are not particularly sensitive to defects in the early stages of disease, and tend to be poorly tolerated by the patient.

As a result of the improvements in sensitivity now offered by the binocular pupillometers of the present invention, it is possible to detect the changes in the eye earlier than with existing techniques. The RAPD measurements can be relied on in a clinical environment, because the housing of the pupillometer means that the accommodation can be controlled, the intensity of the stimulus illumination can be carefully controlled and the results are not subjective to the clinician, as was the case with the previous swinging flashlight test. A skilled clinician using neutral density filters may only have observed RAPD values of greater than 6 dB. With the binocular pupillometers of the present invention, patients presenting with RAPD values of 3 dB or more can be detected with a high degree of sensitivity and specificity (i.e., only a small likelihood of a false positive or false negative). It is recognised in this field that an RAPD of up to 3 dB is within the limits of what is considered to be "normal". The 'between subject variation' for normals is therefore up to 3 dB. It has been shown the device and algorithms used can detect changes with a subject with a precision of +/−6%. Consequently the integrated binocular pupillometers of the present invention can be used to screen for patients which are outside this 'healthy' band and also to determine whether a subject has changed relative to their own baseline with a high level of precision.

As discussed by Lindblom B. in Perimetry update 2002/2003 Publications, 2004; 371-375, a relative afferent pupillary defect is an early sign of optic nerve damage in glaucoma. There is a high likelihood that if such a defect is detected, then the patient will have glaucoma. The improved sensitivity and specificity of the binocular pupillometers of the present invention means that they can be used reliably in a clinical environment in the detection of patients with glaucoma, either as a way of screening patients or as a way of assessing the severity and progression of the condition. Preferably the RAPD is calculated based on modified pupillary response data as discussed above.

According to one aspect, the present invention provides an improved binocular pupillometer that is used to assess the likelihood of primary open angle glaucoma. According to another aspect, the present invention provides an improved binocular pupillometer that is used to assess the severity of primary open angle glaucoma. According to yet another aspect, the present invention provides an improved binocular pupillometer that is used to measure the progression of primary open angle glaucoma.

In the assessment of pupillary response, and in particular RAPD, preferably the stimulating means is adapted to deliver visible light pulses at three (or more) different intensities, for example, spanning the 20 dB range of 0.07 lux to 7 lux, more preferably at intensities of 0.07 lux, 0.7 lux and 7 lux, and the pupillary constriction of each eye is monitored during the light pulses. Processing means may be programmed to deliver a sequence of visible light pulses. Preferably more than five pulses are delivered to each eye at each intensity, more preferably seven or more pulses, usually with the results of the first pulse being discarded. Preferably the amplitude of the pupillary constriction is calculated for each pulse within a set of saved responses, by locating start and finish points during each constriction cycle, e.g., through determining when the rate of change exceeds threshold values, and measuring the difference between the amplitudes at the start and finish points for a given constriction cycle. The pupil diameter may be calculated for a circle or oval which is fitted to a measured pupil area. The amplitude of pupillary constriction for each eye (preferably an average of seven or more values) can be plotted against the stimulus intensity (e.g., the three intensity levels mentioned above on a log scale) to generate a response line. The RAPD can then be calculated by determining the shift between the responses of the left and right eyes, in particular the shift between modified pupillary responses as discussed above. Preferably the responses of the left and right eyes are determined for both direct and consensual stimulation. Preferably a value for RAPD is calculated for both direct stimulation and for consensual stimulation. In one embodiment where RAPD is used to screen subjects into 'healthy' and 'unhealthy' groups, if a calculated RAPD value for either direct or for consensual stimulation is outside a 'healthy' range, then the subject may be put in a group for further assessment or classified as unhealthy. If both the direct and consensual RAPD values show no RAPD or only a small amount of RAPD within the 'healthy' range, then the subject would be classified as 'healthy'.

The pupillary threshold can be found by directly stimulating each eye. The pupillary threshold is defined as the intensity of the stimulus, below which the pupil does not respond to stimulus pulses. As the stimulus intensity is increased, there is a point at which the pupil begins to respond with a constriction reflex. Detection of the pupillary threshold is important in determining the responsivity of the retina, which is important in determining the effectiveness of interventions that may change this, for example in the treatment and detection of Leber Congenital Amaurosis (LCA). This disease can be treated with gene therapy. Measuring the dynamic parameters of the pupil constriction curve can be used to quantify visual impairment and improvement during and after treatment. By employing pupil constriction data in a feedback loop to the stimulus intensity, the stimulus intensity can be modified until the pupillary threshold is determined. In order to provide accurate and precise pupillary threshold measurements, the apparatus must have good sensitivity at low levels of light stimulus and the results obtained must be clinically reliable. This can be achieved using the integrated binocular pupillometers with the improvements described when assessing pupillary threshold in a subject.

Thus the binocular pupillometer of the present invention can also be used in the treatment of conditions like Leber Congenital Amaurosis, Age Related Macular Degeneration and Retinitis Pigmatosa, since it provides a device which generates reliable measurements that are not prone to intraoperative variation but yet the device is sufficiently sensitive to small changes in eye condition that it can be used to monitor the progress of patients. While treating one eye at a time, for example in the treatment of Leber Congenital Amaurosis, the binocular pupillometer of the present invention can be used to monitor the progress of the treatment by accurately measuring pupillary characteristics such as pupillary threshold and/or the change in RAPD with respect to a baseline value.

According to one aspect, the present invention provides an improved binocular pupillometer which is used in the treatment of Leber Congenital Amaurosis. According to another aspect, the present invention provides an improved binocular pupillometer which is used in the treatment of Age Related Macular Degeneration. According to yet another aspect, the present invention provides an improved binocular pupillometer which is used in the treatment of Retinitis Pigmatosa.

The binocular pupillometer referred to in these or other of the various aspects may comprise any or all of the preferred features discussed in this specification.

The binocular pupillometer of the present invention may have other applications, for example, the improved sensitivity and specificity can be of help when monitoring the effects of diabetes, recording pupillary responses of players during video games, determining extent of anaesthesia in a patient, roadside testing of drivers for alcohol or drug use, etc. The equipment is compact and portable allowing it to be used easily in these environments while providing measurements that can be relied on in clinical or legal assessments. The measurements can be taken with or without the cooperation of the person involved and can be compared to reference values for clinical assessment, for example making it particularly suited for determining the extent of anaesthesia in a patient being operated on, or for detecting drug use at the scene of an accident.

As the observed improvements can be seen, in part, to be the result of the improved channel isolation, viewed from another aspect, the present invention can be seen to provide an integrated binocular pupillometer for assessing pupillary response in a subject, the pupillometer comprising a housing containing: stimulating means arranged to apply visible light pulses independently to each eye, sensing means arranged to generate separate pupillary response data in respect of the left and right eyes, and visible fixation means; wherein the visible light applied to the left and right eyes is separated by physical means to reduce the cross-contamination of light to less than 1%. In other words the present invention can be seen to encompass other formats of binocular pupillometer that are used to assess pupillary constriction in response to pulses of visible light, where a barrier is incorporated to reduce the cross-contamination of visible light, i.e. the light intended for one eye being received by another, to less than 1%, preferably substantially less than 1%, for example, less than 0.1%, or even less than 0.01%.

A further significant difference of the present invention is that it offers a binocular pupillometer which is "integrated" in the sense that the eyepieces, the sensing means, the illuminable screens and the visible fixation points are contained within a common housing to define a pupillometer that is readily portable and can be mounted on a desktop or handheld. If desired, the housing may separate into portions for carrying, but more preferably the binocular pupillometer is a single piece item which is ready to use straight out of a carrying case. This is in stark contrast to the binocular pupillometer described by Kalaboukhova et al., which comprises large items of equipment and a dark room.

The sensing means for generating and recording pupillary response data may, for example, comprise means for infrared illumination of each eye, such as infrared-emitting diodes. Infrared illumination applied in this way will be scattered back from the iris and may be transmitted through a suitable optical train to form an image of at least the internal boundary of the iris with the pupil. Detector means which may be used to permit generation of pupillary response data from such images conveniently comprise two-dimensional arrays of charge-coupled devices, e.g. as in CCD video cameras. Separate detectors may be used for each eye or images may be transmitted to separate parts of a common sensor (e.g. as described in WO-A-94/07406) or alternately to the same part of a single sensor (e.g. as described in WO-A-2006/032920).

Pupillary responses which may be detected include depth of constriction, speed of constriction, latency period and redilation time. In a preferred embodiment changes in pupil diameter are recorded; processing of the image data may use techniques such as image enhancement, automatic measurement of pupil area and application of a circle fitting algorithm in case of variation from absolute circularity in pupil shape.

The screen of each of the two stimulating means is preferably illuminable by a light-emitting diode (most preferably a white light-emitting diode) positioned outside the field of view. Such use of indirect light stimulation, as opposed to light stimulation which is shone directly into the eye, has been found to be particularly beneficial in allowing consistent and reproducible results to be obtained. In another embodiment, an array of light sources is provided for illuminating the screen, for example, an array of light-emitting diodes. The array of light sources may supply different colours of visible light, for example, red light, green light, blue light and/or yellow light, the light sources being arranged to illuminate the screen independently with similar levels of light intensity.

The configuration of the screen and object lens such that the observable field of view is at least 9°, e.g. 10±0.5°, more preferably 14° or more, e.g., 20° or more, is also highly advantageous in that it ensures that stimulating light reaches a substantial portion of the retina, including the macular and fovea.

The visible fixation point associated with each illuminable screen is a further key feature of the pupillometer of the invention, significantly enhancing its versatility and the consistency of measurements obtained. Each such point may conveniently comprise a steadily illuminable coloured light source (e.g. a light-emitting diode) positioned in contact with or behind an aperture in the respective screen. The light may be relatively dim compared to the stimulating light. Each fixation point and object lens may be configured such that the fixation point essentially appears at infinity, although systems in which the fixation point may be made to appear nearer to suit a particular subject may also be employed. By locating the visible fixation point on the optical axis and monitoring through the centre of the fixation optics, it keeps possible aberrations to a minimum. It is also envisaged that a common visible fixation point may be provided, which through a shutter arrangement or the like, is only visible to one channel at a particular time.

Aniscoria is a common condition wherein the pupils are of unequal size, and thus will naturally result in unequal illumination. As a result of the improved accuracy and precision, further improvements in the assessment of the patient can be made by taking account of any aniscoria. Thus, preferably the method of calculating RAPD includes the step of comparing the pupil sizes of the left and right eyes without stimulation and determining the amount of reduction in retinal illumination which would result from anisocoria. Preferably the reduction in illumination is calculated from determining a value for the square of the smaller pupil diameter divided by the square of the larger pupil diameter, and more preferably still the negative logarithm of this value is determined. The calculated reduction in retinal illumination may then be taken into account when assessing the RAPD of the patient in order to provide a much more accurate evaluation. Thus when there is an apparent RAPD in the eye with the smaller pupil, preferably the RAPD which is attributable to disease is calculated as the apparent RAPD minus the RAPD caused by the anisocoria. Similarly, when there is an apparent RAPD in the eye with the larger pupil, preferably the RAPD which is attributable to disease is calculated as the apparent RAPD plus the RAPD caused by the anisocoria. The anisocoria can be quantified as a single value by taking the average of each anisocoria correction for each light level, or alternatively separate values for anisocoria correction at each light level can be calculated and used in the dual line RAPD calculation.

Preferred embodiments of the present invention will now be described by way of example only and with reference to the accompanying drawings.

BRIEF DESCRIPTION OF THE DRAWINGS

FIG. 6b is an example of the pupillometer housing and FIG. 6c is a side view of a suitable barrier;

FIG. 7 is a schematic plan view of the optical train for the left eye and indicating the barrier which extends between the left and right channels as well as the foam seal bridging the nose of the patient;

DARK ADAPTATION

The length of dark adaptation is important when measuring RAPD because the retina becomes more sensitive with time, particularly during the first 30 seconds of darkness. A well adapted retina will be very sensitive and require less stimulation to bring about maximum constriction, therefore the saturated part of the pupil response curve will occur at very much lower stimulus intensities. It is therefore important to measure the RAPD at a standard time after dark adaptation has begun. Preferably 30 seconds of dark adaptation is provided before the pupils are stimulated.

Intensity of the Stimulus

The intensity of the stimulus is important in the detection and measurement of the RAPD because the amplitude of the pupillary response is limited by the mechanical range within which the iris can move. In normal, healthy subjects, the maximum pupil size is 8 to 10 mm, whilst the minimum pupil diameter is around 2 mm. Maximum pupil diameter diminishes with age at a rate of approximately 1 mm per decade, from the age of 20 years. The range of mechanical movement of the pupil therefore diminishes with age.

Figure 1:
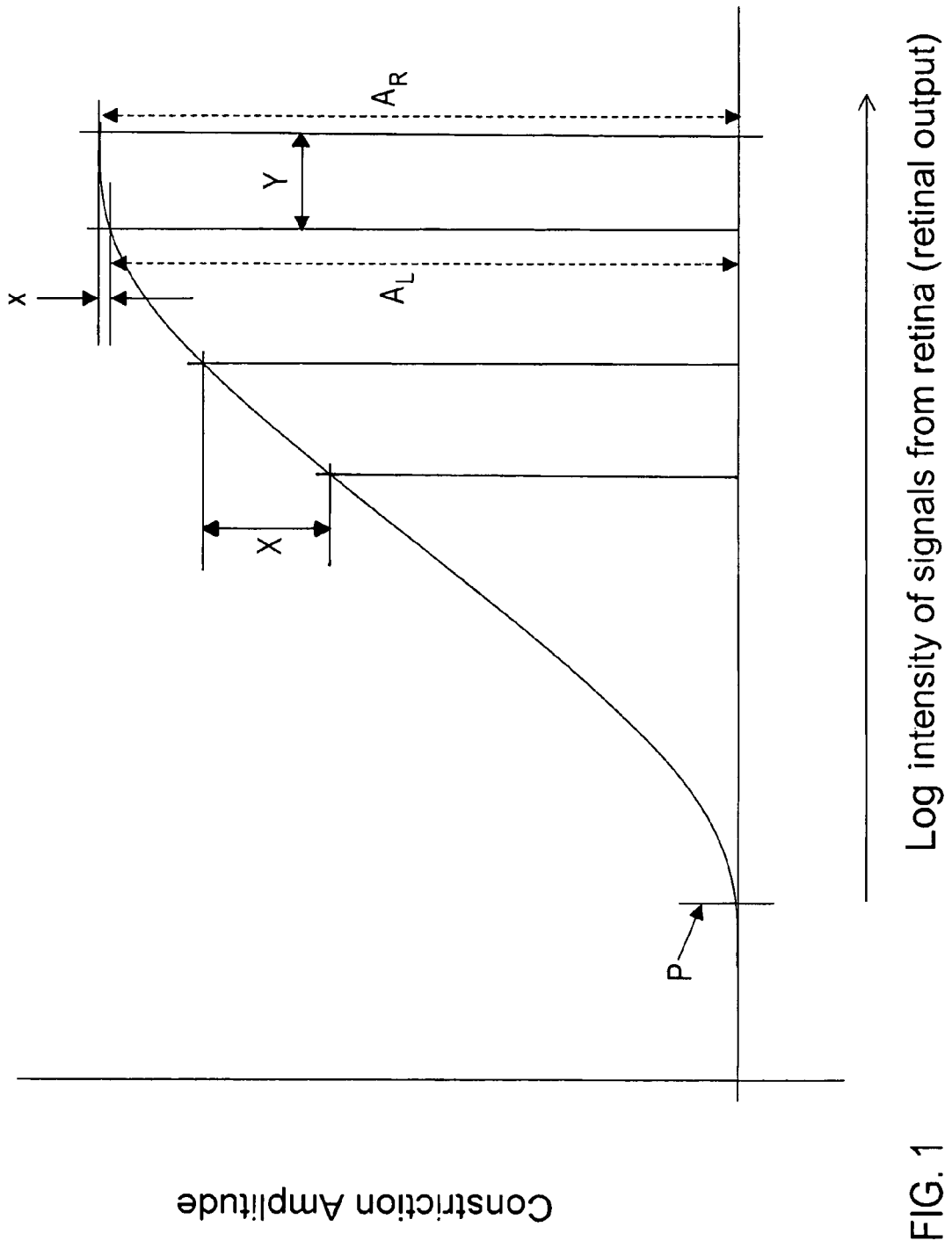
FIG. 1 is a graph showing pupillary constriction amplitude against the log of intensity.

There is a range of light intensities for which the pupil will respond with a reflex constriction. At very low intensities, the pupil will not constrict. This is known as the pupillary threshold. As the intensity of the stimulus increases above the pupillary threshold, the amplitude of constriction increases approximately with the logarithm of the change in intensity. FIG. 1 shows a graph of pupillary amplitude constriction versus the log of intensity with the pupillary threshold marked as point P. This continues until the maximum amplitude of constriction has been reached, beyond which, increasing the stimulus intensity will not bring about any change in pupil constriction. This condition is termed "saturation".

FIG. 1 also illustrates the effect of trying to measure RAPD using stimulus intensity in this saturation region. In the example shown, where the stimulus is very bright, there is only a small difference x in pupillary response between the left and right eyes ($A_L$ and $A_R$ denote the amplitude of the left and right eye responses) despite a large difference X in retinal output, i.e., the intensity of the stimulus signals being observed from the retina. On the other hand, if the stimulus is too dim, i.e., measurements are taken from the flat part at the start of the pupillary response curve, the sizes of the pupillary response are likely to be small and noisy. Thus; using intensities that are either too bright or too dim can cause difficulties in the assessment of RAPD.

Ideally, the stimulus intensity should be located in the more linear region X indicated in FIG. 1, away from the saturation and threshold parts of the curve, in order to generate good pupillary constriction amplitude responses. This allows changes in the pupillary constriction amplitude to be measured with much greater accuracy and sensitivity for a given difference in retinal output.

Since every person's retina is slightly different, giving rise to slightly different responses, there is no specific intensity that will work for everyone. In order to maximise the possibility of stimulating the retina at the correct intensity, it is preferred to stimulate each eye with three stimulus intensities covering a 100-fold (or 20 decibel) range. This range has been found empirically to be between 0.07 lux and 7 lux. The stimulus intensities used are:

| Brightest stimulus: | 7.0 lux | (20 dB) |
| Intermediate stimulus: | 0.7 lux | (10 dB) |
| Lowest stimulus: | 0.07 lux | (~0 dB). |

Calculating RAPD

Figure 2:
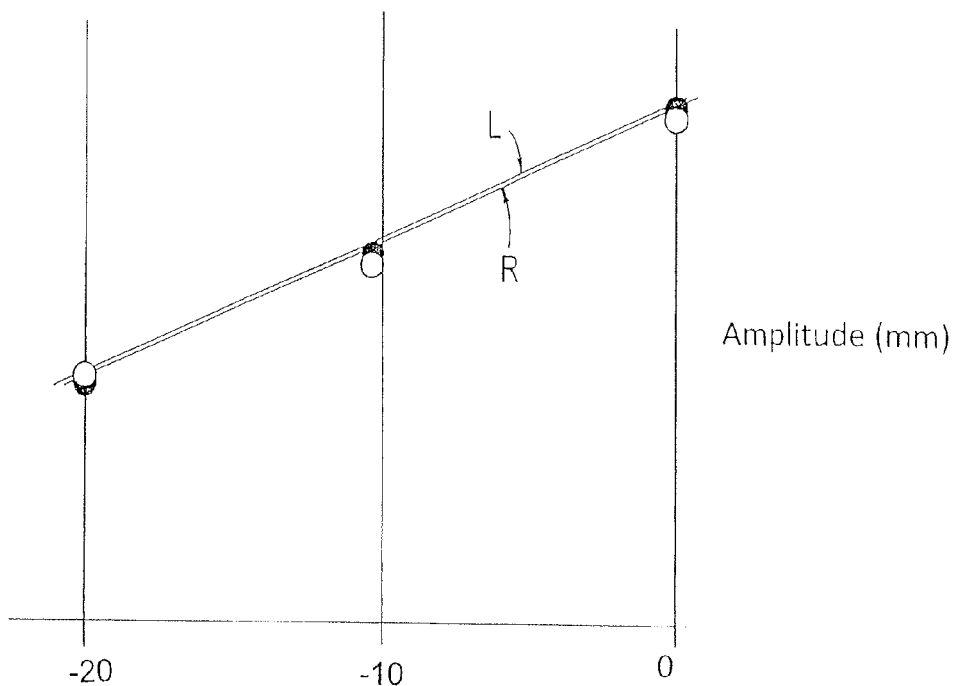
FIG. 2 is a graph showing pupillary constriction amplitude versus stimulus intensity for normal eyes.

The use of several different intensities when calculating RAPD is disclosed in WO 2006/032920. In the case of a healthy patient, there will be no significant difference between the left and right response amplitudes at a given stimulus intensity, as shown in FIG. 2. In the case of a patient with a diseased eye, the stimulation of one eye will have a lower pupillary constriction amplitude response than the other (see FIG. 3) creating a separation between the two, generally linear, responses. WO 2006/032920 teaches how the RAPD can be found by determining the shift along the intensity axis that is required to bring the two profiles into coincidence.

Figure 3:
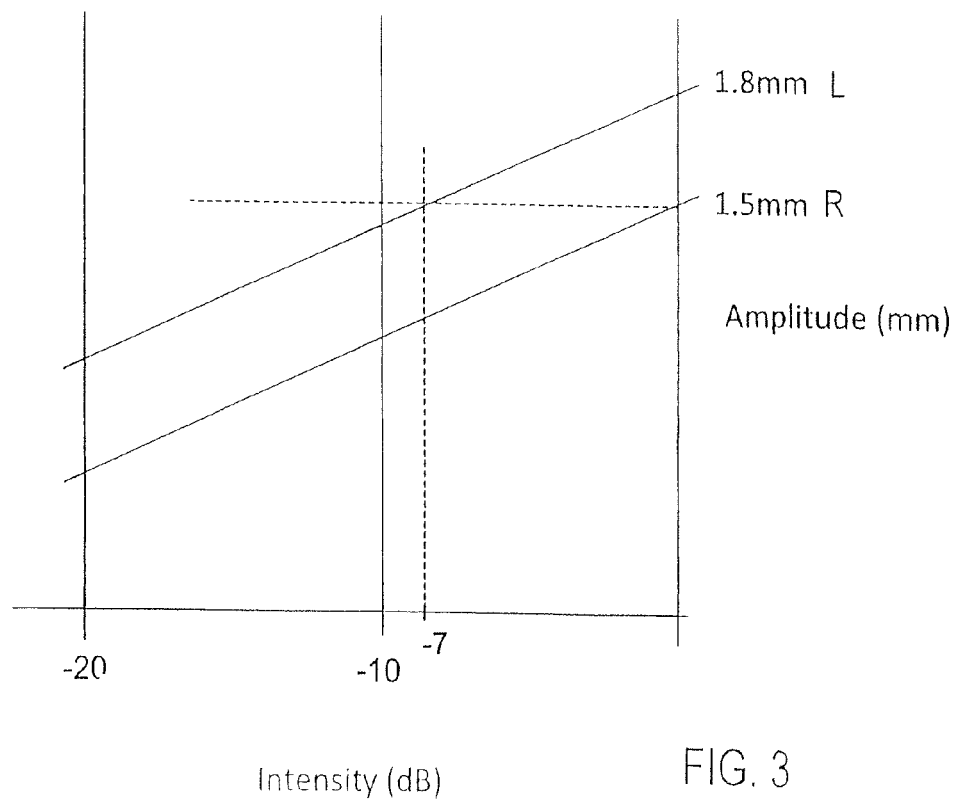
FIG. 3 is a graph showing pupillary constriction amplitude versus intensity for one diseased eye and one normal eye.

In FIG. 3, the intensity for the x-axis is plotted in decibels, which is a logarithmic scale for intensity, In the patient example shown, the responses can be seen to intercept the y-axis (i.e., zero decibels) at pupillary constriction amplitudes of 1.8 mm and 1.5 mm for the left and right eyes respectively. The left eye has to have 7 dB less light than the right to elicit the same (1.5 mm) amplitude response. The right eye in this example has an RAPD of 7 dB.

Figure 4:
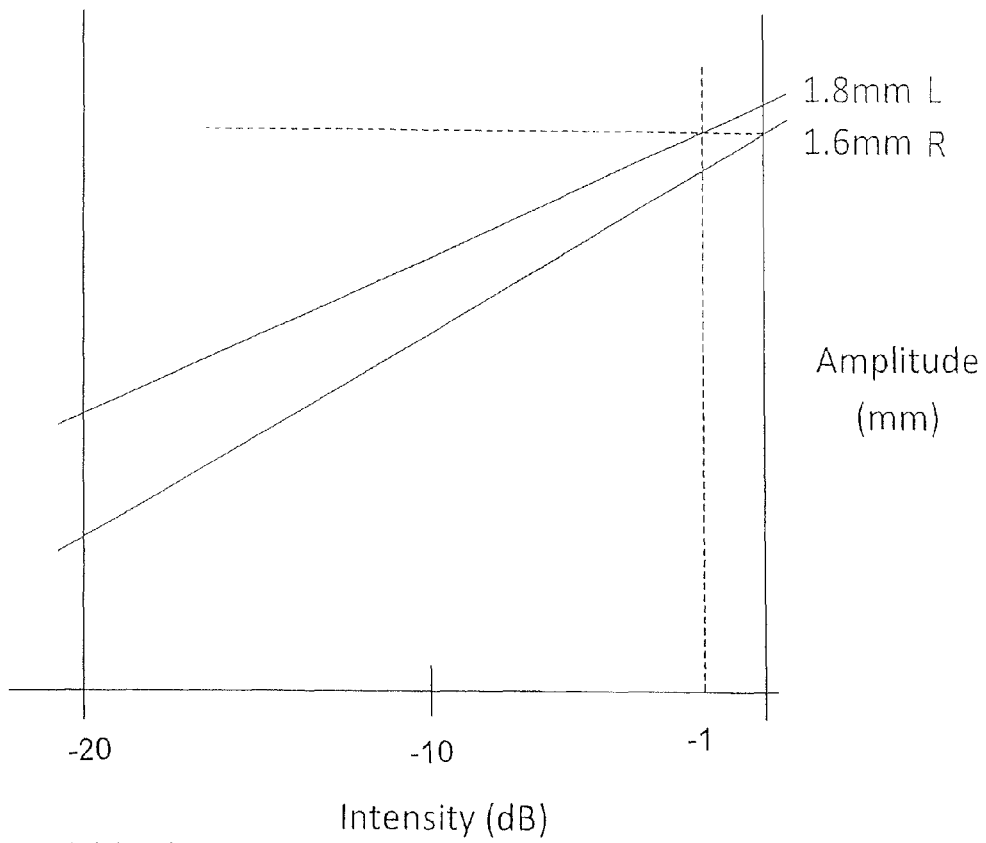
FIG. 4 is a graph illustrating that the pupillary constriction amplitude versus intensity responses are not necessarily parallel.

However, the present inventor has noticed that the amplitude response lines are not always parallel, i.e. the rate of change pupillary response with stimulation intensity for each eye is different. This is shown in FIG. 4 and it can give rise to misleading results. The pupillary constriction amplitude responses now intercept the y-axis zero decibels at 1.8 mm and 1.6 mm for the left and right eyes respectively. Calculating the shift in the responses at this point results in a finding that the left eye needs 1 dB less light to give the same response as the right eye. The right eye would be considered to have an RAPD of 1 dB. However this is misleading.

To solve this problem, the binocular pupillometers incorporate a new algorithm to calculate an 'Area Normalised RAPD', which has been found to give a much more accurate representation of the RAPD in the patient. The Area Normalised RAPD will be discussed in more detail below.

Binocular Pupillometer Apparatus

Figure 5:
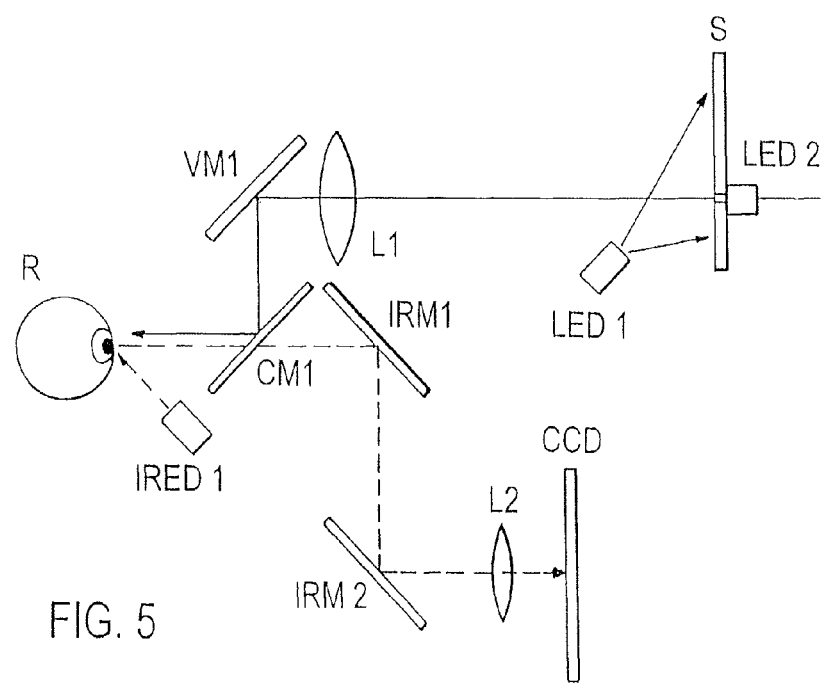
FIG. 5 is a schematic side elevation showing the optical train of a preferred binocular pupillometer according to the invention.

FIG. 5 is a schematic side elevation of a pupillometer according to an embodiment of the invention showing an optical train for the right eye R providing vertical separation of infrared sensing irradiation and visible light stimulation. In this embodiment, sensing infrared light from infrared-emitting diode IRED is scattered from the iris of the right eye R, passes through cold mirror CM1, is reflected by first-surface mirrors M1 and M2 and is focussed by lens L2 onto a CCD imager.

Screen S is illuminable by light-emitting diode LED1 positioned so as to be outside the field of view of the subject. Stimulating light pulses from screen S are transmitted through object lens L1 and reflected by first surface visible mirror VM1 and cold mirror CM1 to the right eye. Green light-emitting diode LED2, positioned behind a small aperture in screen S, provides the visible fixation point, which is positioned at the focal point of object lens L1.

A similar optical train (not shown) is provided for the left eye. It is important that the two trains are optically separated by suitable dividing means in order to avoid cross-contamination of light stimuli to the contralateral. The cross-contamination of light should be less than 1%, preferably substantially less than 1%, for example, less than 0.1%, and even up to a level where there is less than 0.01% cross-contamination.

In operation of the pupillometer according to the invention it is preferred to apply a sequence of stimulating visible light pulses of identical duration, intensity and separation to the left and right eyes alternatively and to measure the amplitude change, e.g. in pupil diameter, caused by these stimuli. Pupillary response may be maximised by selecting a relatively high intensity for the pulses, thereby optimising reproducibility.

The pulse durations are conveniently in the range 0.2-0.5 seconds, with separation times in the range 1-8 seconds, e.g. 1.2-5 seconds. The alternating left and right eye stimuli are preferably symmetrically interleaved.

Accuracy is assisted by recording results for a sequence at 4-8 pulses to each eye, for example 4 pairs of 0.4 or 0.5 second pulses 3 seconds apart (i.e. a sequence 0.4 or 0.5 second left eye stimulus, 3 seconds off, 0.4 or 0.5 second right eye stimulus, 3 seconds off etc.), 7 pairs of 0.2 second pulses 2 seconds apart or, more preferably, 7 pairs of 0.4 second pulses 1.6 seconds apart. This last sequence has been found particularly advantageous in providing optimum precision in measuring pupillary response in a procedure with an overall duration of only about 30 seconds.

It is generally preferred to discard data from the first pair of measurements in such sequences. These tend to be the least accurate since the states of adaptation of the retina to illumination change substantially following the initial pulse to each eye.

Data from the remaining pairs of the sequence may be averaged to provide traces of pupillary response such as plots of the average pupil diameter change induced by the stimuli. It will be appreciated that these may be separated into direct reflex (e.g. as in left pupil response to left stimulus) and consensual reflex (e.g. as in right pupil response to left stimulus). In order to enhance accuracy it is preferred to use only data in respect of direct reflex.

It will be appreciated that such averaging of left and right pupillary responses respectively will smooth out at least some pixel-related noise generated by sensing components such as CCD imagers.

If desired the results may be cleaned of artefactual data caused by blinking. Thus, for example, if a blink is less than three frames in duration (i.e. <3×0.04 seconds at an imaging frame rate of 25 Hz), one may interpolate "good" data from either side of the blink. This may be performed manually or by appropriately programmed electronic processing.

The amplitudes $A_R$ and $A_L$ of the pupil diameter changes for the right and left eyes may be normalised by dividing them by the initial (i.e. unstimulated) pupil diameters $(Di)_R$ and $(Di)_L$. An afferent pupillary defect is present where the two normalised amplitudes differ, lying in the direction of whichever is the smaller. It may be qualified by the formula $$APD(\text{or 'RAPD'}) = 100 \frac{(1 - \text{smaller normalised amplitude})}{\text{larger normalised amplitude}} \%$$

In order to optimise the results one may advantageously perform at least two sets of measurements and calculations so as to obtain two or more APD values. Thus, for example, it is currently preferred to generate three APDs, take the closest two values and reject the third. The final APD is the mean of these two, whilst their standard deviation is a measure of repeatability.

The APD can also be presented in dB, since the response of the pupil to stimuli is logarithmic. As mentioned above, the standard method of assessing APD clinically, without an objective pupillometer, is the swinging flashlight technique in which a small pen-torch is moved from eye to eye, and the pupil responses compared by the clinician. If there is a notable difference in the two eyes, the clinician will try to neutralise this difference by attenuating the light to the more strongly responding eye the reference eye) with different strengths of neutral density filter. These filters are available in 1 dB increments.

The pupillometer of the present embodiment has a slot in front of each stimulus, one for the left, one for the right eye, which is capable of allowing a neutral density filter to be positioned between the stimulus and the eye at which that stimulus is directed. The RAPD can be monitored continuously, and filters of varying strength can be positioned until the average APD is zero. The final filter is a measure, in dB of the APD deficit in the affected eye.

To automate the measurement of RAPD in dB, it is possible to use the fact that the software driving the stimulus LED uses a digital value between 0 and 2048 to modify the intensity of the stimulus. Calibrating the digital values can be achieved by measuring the luminance produced by each digital value, and the equivalent attenuation produced by the filters, when different neutral density filters are placed in front of it. A simple look-up table can be produced for each device (since all stimulus LEDs have a variation in characteristic caused by the manufacturing processes involved in their production). The software is programmed to mimic the current clinical practice of variation of neutral density strength, and whilst averaging the RAPD measurement in response to any given intensity, can modify the intensity iteratively in the reference eye until a balance in pupil response between the two eyes has been achieved. By outputting RAPD values in decibels, this helps the clinician to have a better understanding of the response data since the clinician will already understand these values from the traditional swinging flashlight test and the values of the neutral density filters.

Figure 6A:
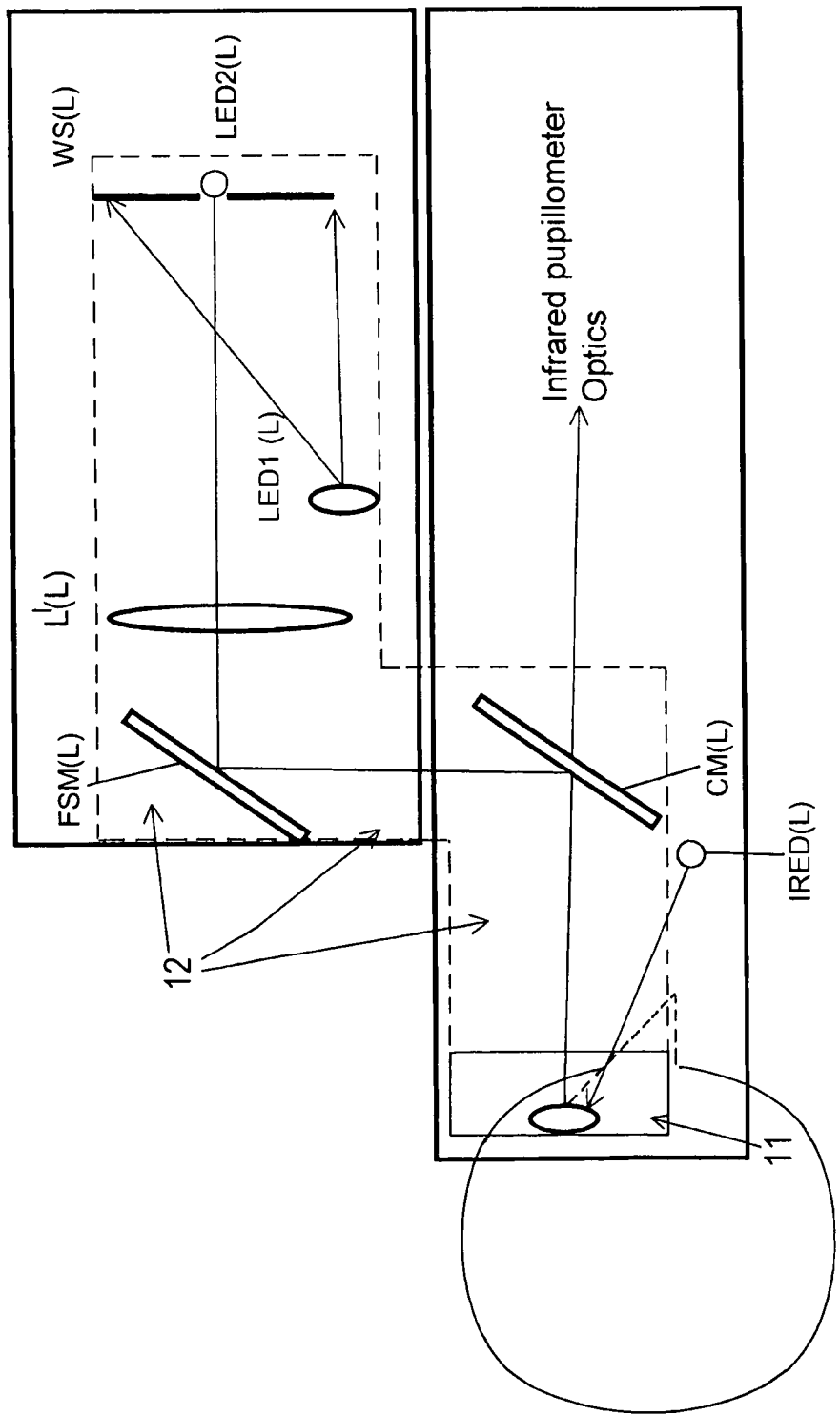
FIG. 6a is a side elevation of a preferred optical train for one channel of a preferred binocular pupillometer illustrating the position of the barrier with respect to the left and right stimulation channels.
Figure 8:
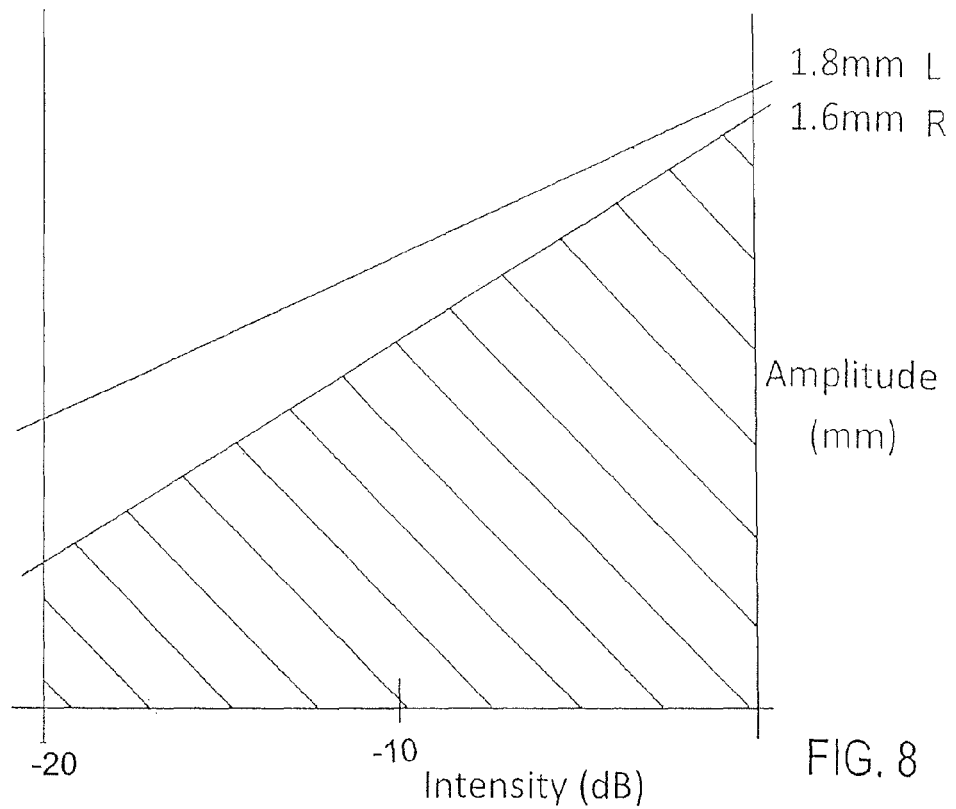
FIG. 8 is a graph illustrating the area under the recorded pupillary response for one eye.

FIG. 6a is a schematic side elevation of a preferred binocular pupillometer, which is similar in many respects to that of the embodiment of FIG. 5 but also shows the extent of the dividing means between the stimulus channels. Thus, in the pupillometer of FIG. 6a the optical trains providing the light stimulus to the eyes are separate and duplicated for both the left and right sides. White screen WS(L) is illuminable by light-emitting diode LED1(L) in a similar manner to FIG. 5. Stimulating light pulses from screen WS(L) are transmitted through object lens L1(L) and reflected by visible, flat surface mirror FSM(L) and cold mirror CM (L) to the left eye. Green light-emitting diode LED2(L), positioned behind a small aperture in screen WS(L), provides the visible fixation point, which is positioned at the focal point of object lens L1(L). These elements are duplicated for the right eye. The dashed lines indicate the position of the physical barrier 12 between the left and right channels.

The sensing optics for the left eye are shown in FIG. 6a and comprise infrared light-emitting diode IRED(L) arranged to scatter sensing infrared light from the left eye, which then passes through cold mirror CM(L). First-surface mirrors IRM1 and IRM2 and lens L2 are also provided though not shown, and operate in the same manner as the corresponding elements of FIG. 5. Preferably a set of one infrared emitting diode IRED1, one cold mirror CM1, one first-surface mirror IRM1, one first-surface mirror IRM2 and one lens L2 is provided for each eye. The first-surface mirrors IRM1 and IRM2 in such an arrangement may form a periscope that can be tilted slightly about an axis of the lens L2. The tilting motion of the left periscope can be coupled to the right periscope using toothed wheels to create a similar but opposite movement. In this way it is possible to reduce or increase the separation of the first-surface mirrors IRM1 for accommodating small or large interpupillatory distances. However other infrared pupillometer optics beyond the physical barrier between the left and right stimulus channels are also possible, for example two infrared detectors could be used or the infrared light could be directed to different areas of the same detector.

The housing 1 of the binocular pupillometer (see FIG. 6b) comprises two shells 2 moulded from plastics that form the left and right sides of the pupillometer which meet at a midway point (e.g., the middle, vertical plane of the pupillometer when it is mounted on a table ready for use). Additional panels may be provided to allow access to certain regions of the pupillometer. The shells are provided with internal formations for holding the internal components in position (not shown). The shells also include an internal partition 3 extending between the left and right sides that defines a first pocket 4 for the stimulating optics 5 and a second pocket 6 for the sensing optics 7. The internal partition 3 can also retain a cold mirror CM(L) for each channel, the cold mirror CM(L) only allowing infra-red light through to the second pocket 6 and the sensing optics 7. An eye-piece 8 is provided for the subject to view the light pulses generated by the stimulating optics 5. Other partitions such as partition 3' may be provided to accommodate further components like a processor or power supply 8.

FIG. 6c shows a side view of the barrier 12 (the dividing means) that isolates the stimulating channels. The barrier 12 is preferably a sheet of dark material, such as plastic or card, that has been cut accurately to follow the internal profile of the first pocket 4 and which fits neatly between the two shells 2 of the housing 1 in the assembled pupillometer.

As shown in FIG. 7, which is a schematic view from above of a preferred binocular pupillometer, face foam 10, nose foam 11 and channel isolation barrier 12 are provided to ensure perfect isolation of light between the left and right stimulus channels. The face foam and nose foam is made of a grey/black foam. The nose foam is provided right up to the bridge of the patient's nose to prevent light seeping out across the bridge of the nose. As with the previous figures, WS indicates the white screen, which is illuminated by an illumination light-emitting diode LED1. A fixation light-emitting diode, LED2, is provided on the optic axis behind the white screen WS. L denotes a fixation lens, FSM a face surface mirror and CM a cold mirror. Only the left (L) channel is shown. In practice, all the optics would be duplicated for the right (R) channel.

Thus as it can be seen, the duplicate optics for each eye are advantageous since the channels are completely isolated.

In operation of the pupillometer of this embodiment it is preferred to apply a sequence of stimulating light pulses at three or more intensities covering a 100-fold (20 dB) range. This has been found empirically to be between 0.07 lux and 7 lux. The brightest stimulus is therefore 7.0 lux, the intermediate 0.7 lux and the dimmest 0.07 lux. The stimulating pulses are applied separately and alternately to each eye. The amplitude, i.e. the pupil diameter, caused by these stimuli, is measured.

Area Normalised RAPD Calculation

A method of finding the RAPD according to an embodiment of the present invention is now described with respect to the example of FIGS. 8 to 13. This is denoted the "Area Normalisation" method.

Figure 9:
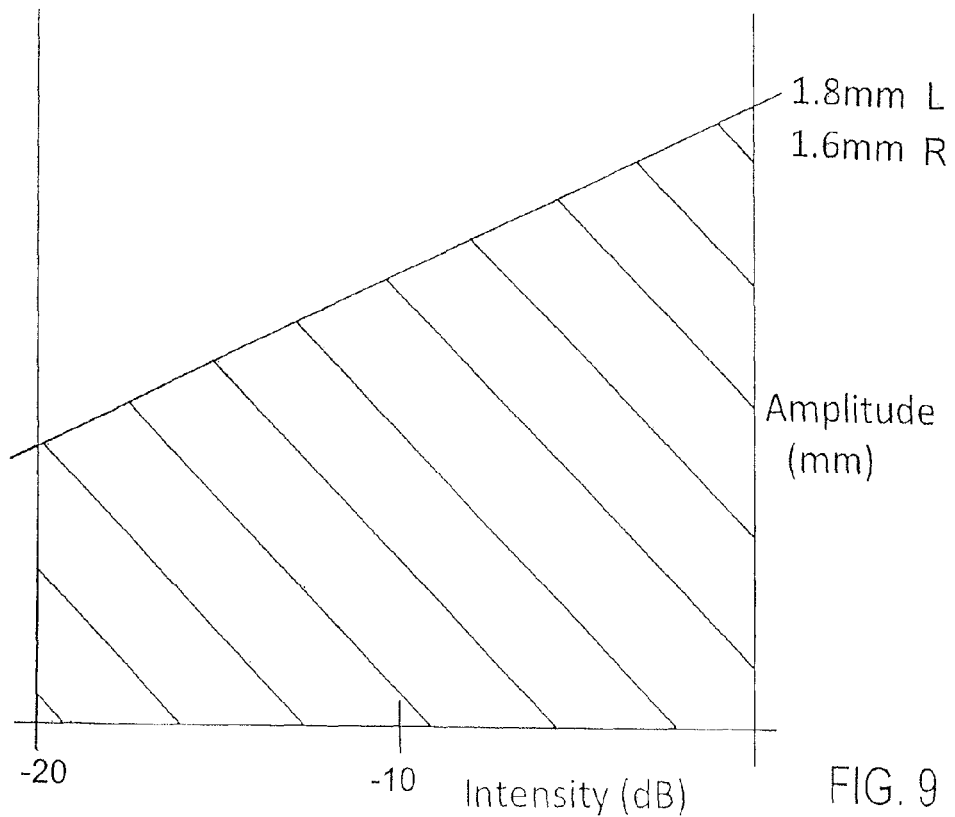
FIG. 9 is a graph illustrating the area under the recorded pupillary response for the other eye.
Figure 10:
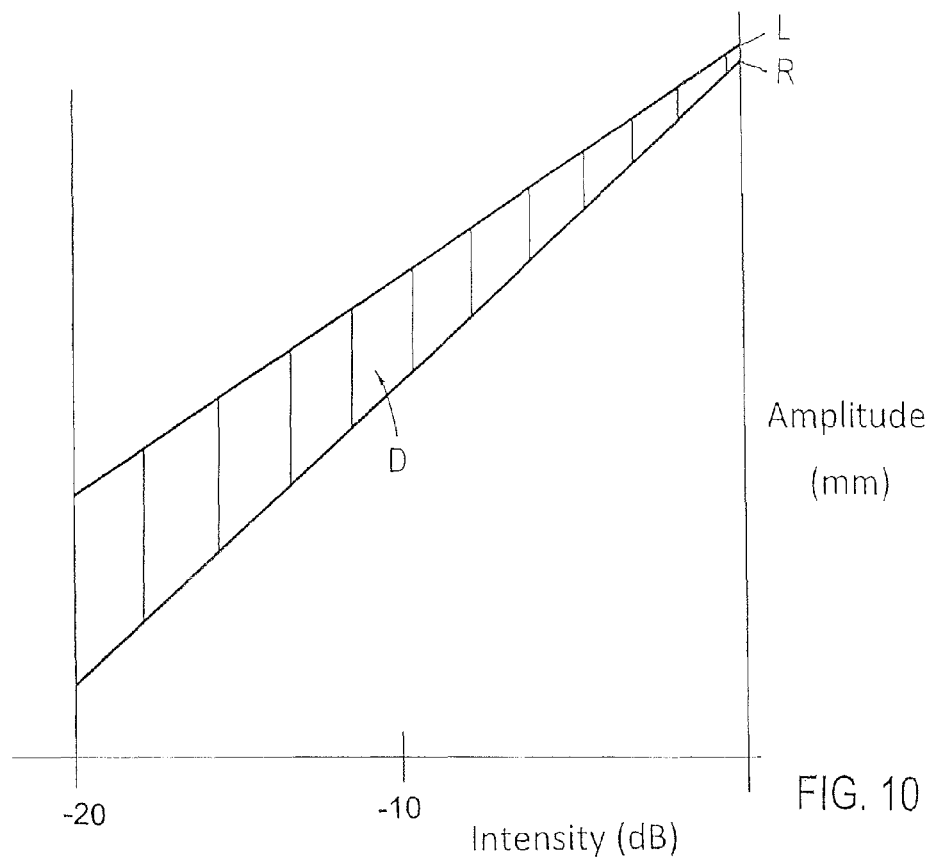
FIG. 10 is a graph illustrating the difference, D, in area between the recorded pupillary responses of the left and right eyes.
Figure 11:
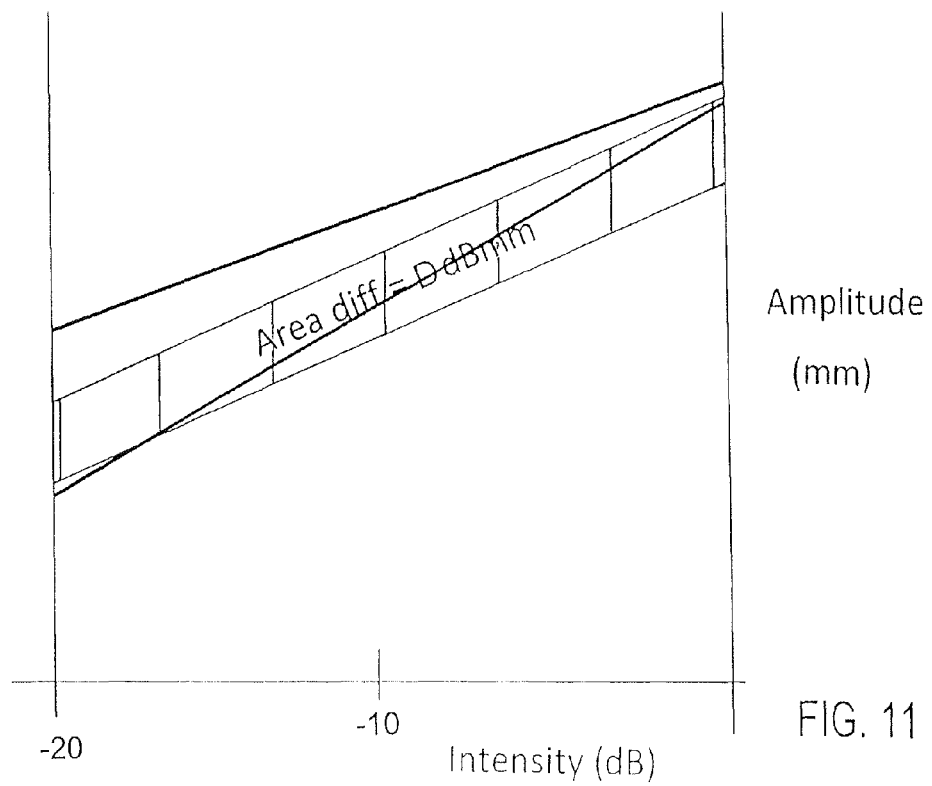
FIG. 11 is a graph illustrating an area equal to the difference between the apparent pupillary responses of the left and right eyes, plotted as a parallelogram having a new slope which is equal to the mean of the left and right apparent pupillary responses.

The area under the right pupillary response is found by integrating the amplitude with respect to the intensity, between the limits of 20 dB (the brightest stimulus of 7.0 lux) and zero decibels. This area is effectively proportional to the "energy of the response" for the right eye, see FIG. 8. In this case it is 30 dBmm. Then the area under the left pupil's response is found in the same way and in this example it is 50 dBmm (FIG. 9). The difference D between these areas is found, which here is 20 dBmm (illustrated graphically in FIG. 10).

Figure 12:
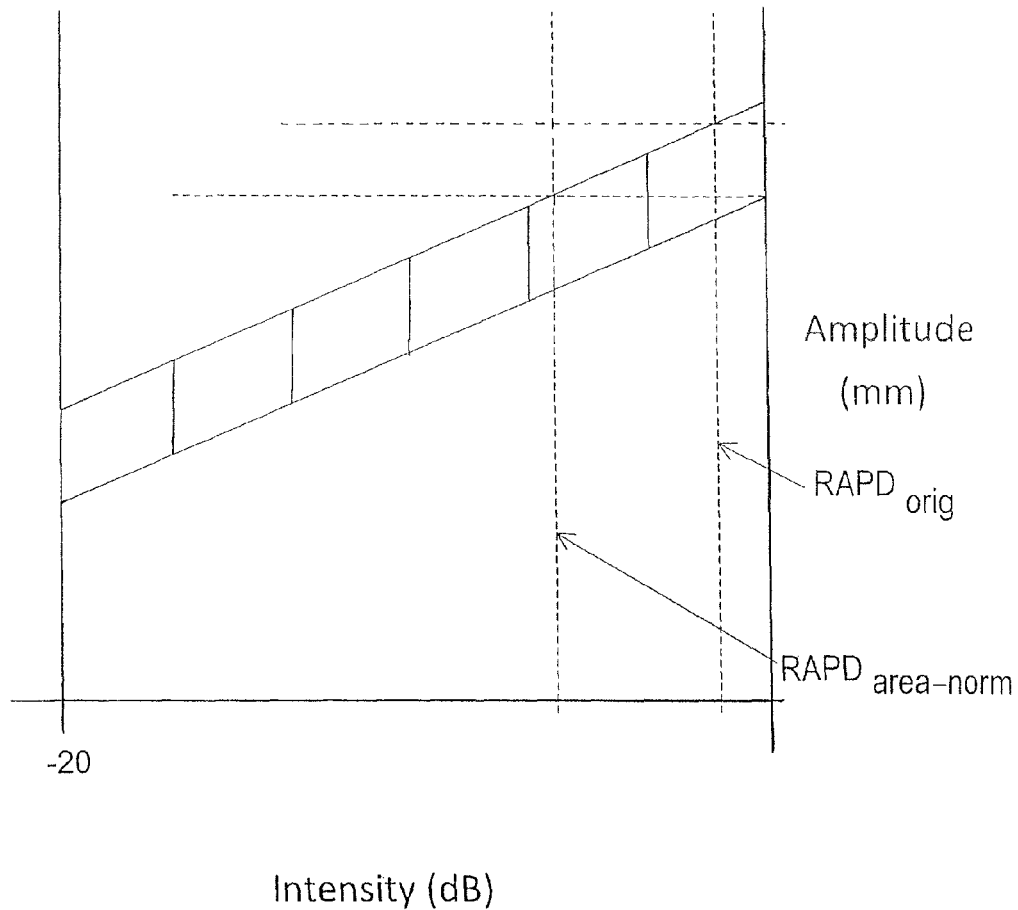
FIG. 12 is a graph of pupillary constriction amplitude against intensity showing the parallelogram of the modified pupillary response and indicating the relative positions of the original misleading RAPD and the new RAPD value based on the average over the whole intensity range.
Figure 13:
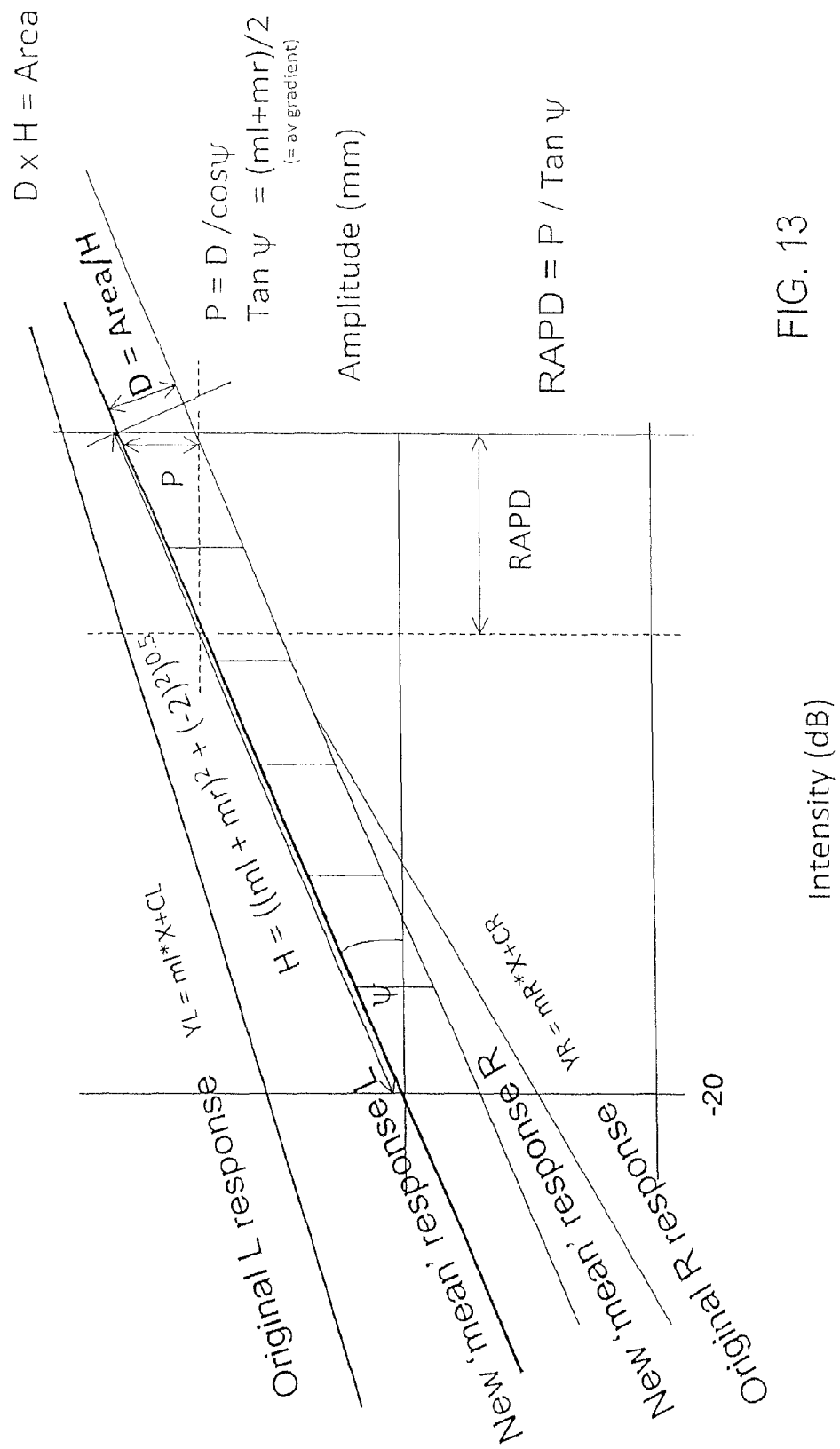
FIG. 13 is a graph illustrating the apparent pupillary responses of the left and right eyes compared to the new modified pupillary responses, and indicating the calculation of RAPD.

First, the pupillary constriction amplitude responses are plotted against intensity as shown in FIG. 4. In the figure, the upper response was recorded for the patient's left eye and the lower response for the patient's right eye. The area under the right pupillary response is found by integrating the amplitude with respect to the intensity, between the limits of 20 dB (the brightest stimulus of 7.0 lux) and zero decibels. This area is effectively proportional to the "energy of the response" for the right eye, see FIG. 8. In this case it is 30 dBmm. Then the area under the left pupil's response is found in the same way and in this example it is 50 dBmm (FIG. 9). The difference D between these areas is found, which here is 20 dBmm (illustrated graphically in FIG. 10). The mean of the left and right slopes is found and the area is projected into a parallelogram having this slope and an area corresponding to the difference D between the areas under the left and right slopes, here 20 dBmm. Effectively the two original lines have been adjusted to be parallel, keeping the area (difference in response) fixed (see FIG. 11). The RAPD can then be found by determining the shift along the intensity axis that is required to bring the two profiles into coincidence. This is essentially an "average RAPD" over the whole intensity range. FIG. 12 is a schematic representation illustrating the difference between the original RAPD ($RAPD_{orig}$) calculated from the apparent pupillary responses of the left and right eyes, and the new "average RAPD" taken over the whole intensity range using the Area Normalisation RAPD calculation mentioned above ($RAPD_{area-norm}$).

Figure 15:
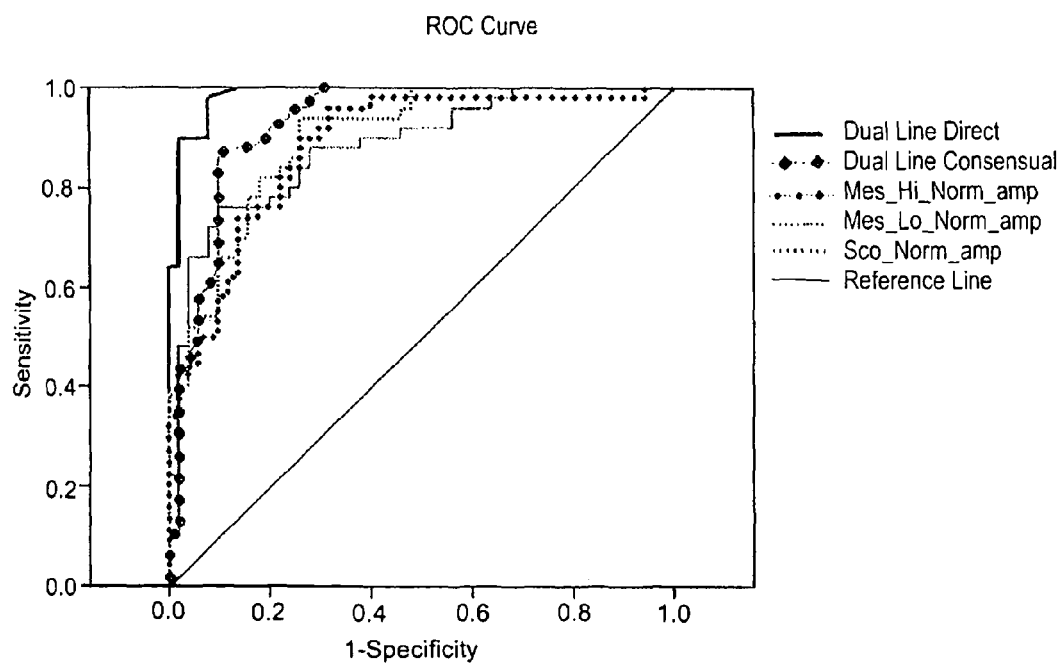
FIG. 15 illustrates Receiver Operator Characteristic curves showing 1-specificity versus sensitivity when Normalised RAPD values are calculated.

Considering this mathematically, referring to FIG. 15, the original response of the left eye can be denoted:

$$YL = ml*X + CL$$

Whilst the original response of the right eye can be denoted:

$$YR = mr*X + CR$$

The RAPD needs to be found which=$P/\tan \Psi$

This can be determined by using the trigonometric relationships of the parts which are already known.

The area of the parallelogram is equal to the length H of the long sides multiplied by the perpendicular distance D between the long sides.

Thus, the area=D×H, and $H=((ml+mr)^2+(-2)^2)^{0.5}$

The area can be found from knowing the pupillary responses of the left and right eyes, integrating to determine the areas under the responses, and subtracting to reveal the area A. The perpendicular distance between the long sides is therefore $$D = A/H$$
$$= A/((ml+mr)^2 + (-2)^2)^{0.5}$$

P, the vertical distance between the two long sides, can be found from:

$P=D/\cos \Psi$, where $\Psi=(ml+mr)/2$=average gradient/2

$RAPD=P/\tan \Psi = \{D/\cos((ml+mr)/2)\}/\tan((ml+mr)/2)$

Figure 14:
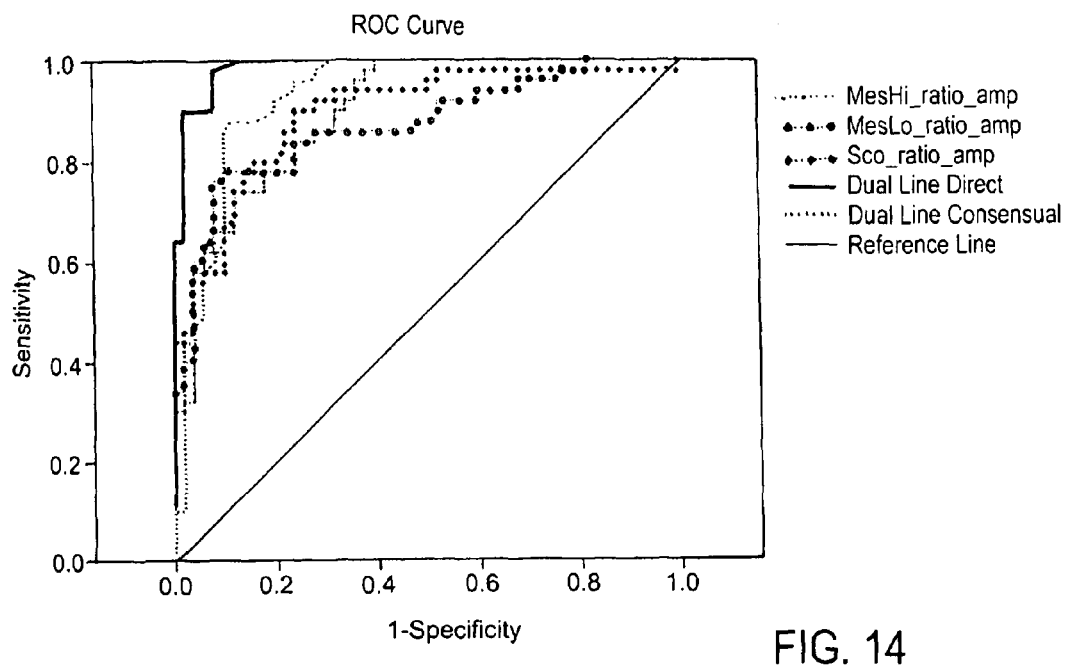
FIG. 14 illustrates Receiver Operator Characteristic curves showing 1-specificity versus sensitivity when Absolute RAPD values are calculated.

The inventor has evaluated this "Area Normalisation" method in relation to prior art methods of determining the RAPD. A sample size of 50 patients was used. FIG. 14 illustrates Receiver Operator Characteristic curves (or ROC curves) showing curves of 1-specificity versus sensitivity for subjects where the absolute RAPD is calculated according to the manner described in WO 2006/032920. The curves show the variation for the Absolute RAPD in subjects under three conditions of: (a) bright stimulus (high mesopic—MesHi_ratio_amp); (b) intermediate light (low mesopic vision where there is a combination of scotopic and photopic vision—MesLo_ratio_amp); and (c) low light (scotopic vision where vision is exclusively through rod cells rather than cone cells—Sco_ratio_amp). The Absolute RAPD values were calculated using:

Absolute RAPD=(1−(smaller amplitude/larger amplitude))×100%

As can be seen, the Absolute RAPD has a reasonable degree of sensitivity and specificity with the curves following close to the top left corner of the plot and being spaced away from the reference line. The greater the area underneath the ROC curve, the better the sensitivity and specificity of the test, i.e., the closer the area is to 1.0, the better.

However, also shown in FIG. 14 are the ROC curves for the RAPD values calculated using the new Area Normalised Method discussed above, labelled as "Dual Line Direct" and "Dual Line Consensual". The Dual Line Direct technique is the Area Normalised Method as applied to the pupillary amplitude responses under direct stimulation, i.e., the contraction of the pupil in the eye which is being stimulated, and the Dual Line Consensual technique is the Area Normalised Method as applied to the pupillary responses obtained under consensual stimulation, i.e., when the opposite eye is being stimulated to the one which is being observed. The ROC curves for these values, particularly the Dual Line Direct values, are pressed even closer towards the top left corner of the plot and accordingly this illustrates the improved sensitivity and specificity that can be achieved with using the new Area Normalised Method of the present invention.

Table 1 illustrates the calculated areas under the various curves shown in FIG. 14. As can be seen, the "Dual Line Direct" and the "Dual Line Consensual" curves have an area which is closer to 1, hence indicating greater sensitivity and specificity.

FIG. 15 illustrates the effect of calculating the Normalised RAPD value for (a) bright stimulus (Mes_Hi_Norm_amp), (b) medium light (Mes_Lo_Norm_Amp) and (c) Low light stimulus (Sco_Norm_amp) on the ROC curves. The Normalised RAPD is calculated using:

$$\text{Normalised } RAPD = \frac{(1 - \text{smaller amplitude/smaller initial diameter})}{\text{larger amplitude/larger initial diameter}} \times 100\%$$

FIG. 15 also includes the ROC curves for the new Area Normalisation Method as a comparison (Dual Line Direct and Dual Line Consensual). As can be seen, the new Area Normalisation Method provides improved sensitivity and specificity over the Normalised RAPD values, particularly when observing the direct stimulation.

Table 2 illustrates the calculated areas under the various curves in FIG. 15.

Figure 16:
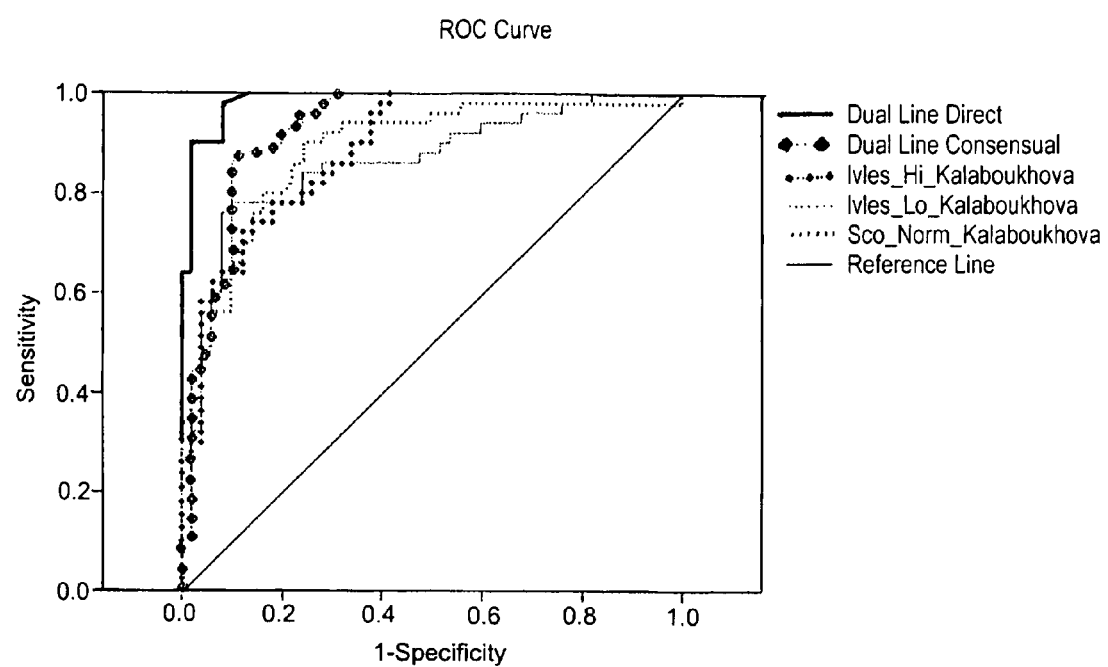
FIG. 16 illustrates Receiver Operator Characteristic curves showing 1-specificity versus sensitivity for RAPD values calculated using the technique, taught by Kalaboukhova et al.

As a comparison, FIG. 16 illustrates ROC curves for RAPD values calculated according to the method described in Kalaboukhova et al, where:

RAPD=((larger amplitude/smaller amplitude)−1)× 100%

The ROC curves are shown for (a) bright stimulus (Mes_Hi_Kalaboukhova), (b) medium light (Mes_Lo_Kalaboukhova) and (c) Low light stimulus (Sco_Norm_Kalaboukhova) respectively. In addition, on FIG. 16 the ROC curves for the new Area Normalisation Method are shown (Dual Line Direct and Dual Line Consensual) for comparison. Again it can be seen that the new Area Normalisation Method, in which all three light levels contribute to the resultant RAPD unlike the other ratiometric methods, generates RAPD values that exhibit improved sensitivity and specificity, providing a much more useful diagnostic tool.

Table 3 shows the calculated areas under the various curves shown in FIG. 16.

Calculating Pupillary Threshold

Pupillary threshold is calculated by determining the intensity at which a stimulus pulse first starts to elicit a pupillary constriction. The difficulty is deciding when the low level of light stimulus has caused a pupillary response or whether the constriction is 'pupillary hippus'—random small variations in pupil size which are thought to be caused by the influences of the higher centres of the brain on the pupillo-motor drive neurones in the mid brain.

Starting with zero stimulus intensity, the pupil is monitored for 1 period of 10 seconds prior to the stimulus pulse being applied, monocularly to each eye. The average

TABLE 1

Area Under the Curve

| Test Result Variable(s) | Area | Std. Error[a] | Asymptotic Sig.[b] | Asymptotic 95% Confidence Interval ||
|---|---|---|---|---|---|
| | | | | Lower Bound | Upper Bound |
| MesHi_ratio_amp | .897 | .030 | .000 | .838 | .956 |
| MesLo_ratio_amp | .869 | .036 | .000 | .798 | .941 |
| Sco_ratio_amp | .893 | .032 | .000 | .830 | .957 |
| Dual Line Direct | .986 | .009 | .000 | .969 | 1.003 |
| Dual Line Consensual | .928 | .027 | .000 | .875 | .981 |

TABLE 2

Area Under the Curve

| Test Result Variable(s) | Area | Std. Error[a] | Asymptotic Sig.[b] | Asymptotic 95% Confidence Interval ||
|---|---|---|---|---|---|
| | | | | Lower Bound | Upper Bound |
| Dual Line Direct | .986 | .009 | .000 | .969 | 1.003 |
| Dual Line Consensual | .928 | .027 | .000 | .875 | .981 |
| Mes_Hi_Norm_amp | .882 | .034 | .000 | .815 | .948 |
| Mes_Lo_Norm_amp | .883 | .033 | .000 | .818 | .948 |
| Sco_Norm_amp | .898 | .030 | .000 | .839 | .956 |

The test result variable(s): Dual Line Direct, Dual Line Consensual has at least one tie between the positive actual state group and the negative actual state group. Statistics may be biased.
[a]Under the nonparametric assumption
[b]Null hypothesis: true area = 0.5

TABLE 3

Area Under the Curve

| Test Result Variable(s) | Area | Std. Error[a] | Asymptotic Sig.[b] | Asymptotic 95% Confidence Interval ||
|---|---|---|---|---|---|
| | | | | Lower Bound | Upper Bound |
| Dual Line Direct | .986 | .009 | .000 | .969 | 1.003 |
| Dual line Consensual | .928 | .027 | .000 | .875 | .981 |
| Mes_Hi_Kalaboukhova | .890 | .031 | .000 | .829 | .951 |

TABLE 3-continued

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Mes_Lo_kalaboukhova | .864 | .037 | .000 | .791 | .937 |
| Sco_Norm_Kalaboukhova | .885 | .034 | .000 | .818 | .952 |

The test result variable(s): Dual Line Direct, Dual Line Consensual, Sco_Norm_Kalaboukhova has at least one tie between the positive actual state group and the negative actual state group. Statistics may be biased.
[a]Under the nonparametric assumption
[b]Null hypothesis: true area = 0.5 and 95% confidence intervals of this ten second pre-stimulus data are calculated. If, after ten seconds plus a latency period of between 150 ms and 700 ms, more than three consecutive pupil measurements which are below the lower 95% confidence interval are found, the first breach of the confidence interval, in a decreasing direction, is marked as the beginning of a pupillary constriction. Should such a constriction not be found, the light intensity is increased by 0.1 dB and the cycle is repeated until a constriction is detected.

Correcting for Anisocoria

Anisocoria, or unequal pupil size, is a common condition. Its presence can be an indication of a life threatening condition, such as Horner syndrome, or something completely benign. However, its presence means that there will be a difference in retinal illumination as a result of the anisocoria. This difference is proportional to the square of the smaller pupil diameter divided by the square of the larger pupil diameter. When plotted in decibels, the reduction in illumination is equal to the negative log of the square of the smaller diameter divided by the square of the larger diameter. In other words:

$$\text{Reduction} = -\log(d^2/D^2)$$

where d and D are the diameters of the smaller and larger pupils respectively.

It follows therefore that on a patient with a smaller right pupil size, if there is an apparent RAPD on the right, then some of this may be attributable to the anisocoria and the reduction in illumination. The RAPD attributable to disease is therefore equal to the apparent RAPD in the right eye minus the RAPD caused by the anisocoria. Similarly if there is an apparent RAPD on the left eye, the RAPD attributable to disease is equal to the apparent RAPD in the left eye plus the RAPD caused by the anisocoria. Taking account of the anisocoria in the RAPD measurement can significantly improve the clinical assessment of the patient.

The anisocoria correction in dB can be dealt with as a single quantity by taking the average of each anisocoria correction for each of the three light levels, or, alternatively, can be dealt with separately for each light level. For example, if the right pupil is smaller than the left, and it receives less illumination than the left eye, for example, as follows:

scotopic level (0.07 lux) right eye receives 0.12 dB less than the left;

low mesopic (0.7 lux) right eye receives 0.11 dB less than the left;

high mesopic (7.0 lux) right eye receives 0.10 dB less than the left.

We can either say on average the right eye receives 0.011 dB less than the left or substitute in the dual line RAPD calculation for the right eye the following light levels:

0 dB (Hi Mesopic) becomes 0 dB+0.1 dB=0.1 dB 10 dB (low mesopic) becomes −10 dB+0.11 dB=−9.89 dB 20 dB (scotopic) becomes 20 dB+0.12 dB=−19.88 dB Optimising Sensitivity and Specificity The binocularity of the pupillometer provides two measurements: the direct RAPD and the consensual RAPD. Each of these has its own set of measurements, which are treated separately.

Combining these two tests, we arrive at a final test which is in essence more sensitive than individual tests. A normal subject is given a true negative outcome if both direct and consensual RAPDs are negative. A patient is given a true positive outcome if either direct or consensual RAPDs are positive.

The ROC curves mentioned previously were obtained by comparing the Normal 0 dB response with the Normal 3 dB (i.e., 0.3 B) response (the accepted amount of neutral density occlusion signifying disease). To make further improvements when assessing patients we compare the results from the normals at 0 dB neutral density filter (the baseline 'Normal' response) with the patient's responses (patients were not subjected to neutral density filters, because they all had occlusion anyway).

Figure 17:
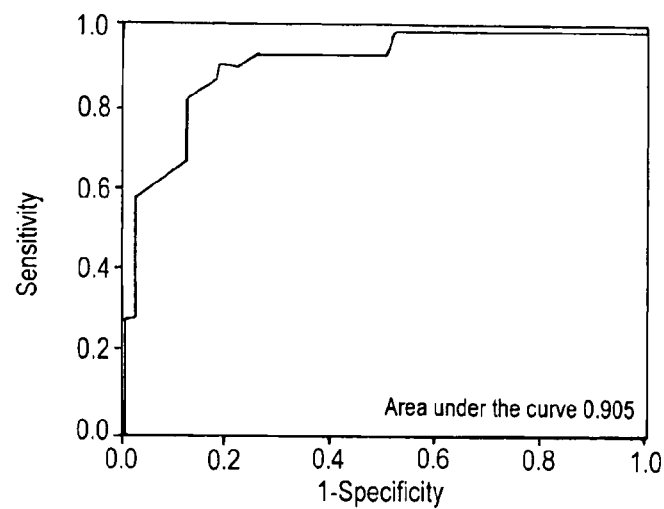
FIG. 17 illustrates the Receiver Operating Characteristics (ROC) curve analysis for differentiating normal subjects from glaucoma patients.
Figure 18A:
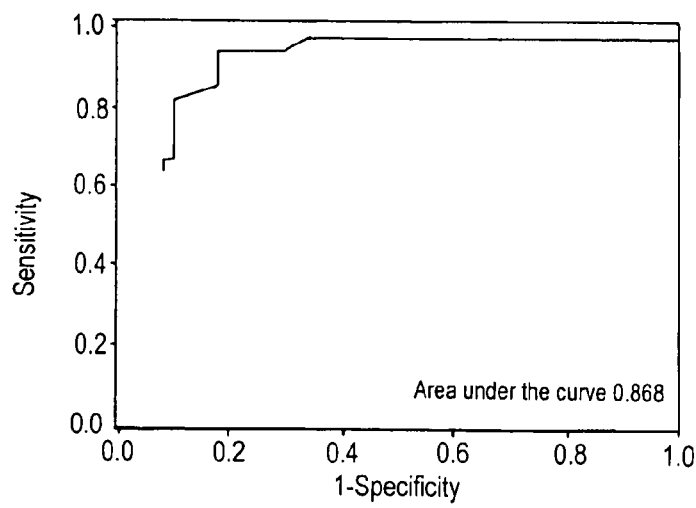
FIGS. 18(a) and 18(b) describe ROC curve analysis for $RAPD_{DIR}$ and $RAPD_{CONS}$.
Figure 18B:
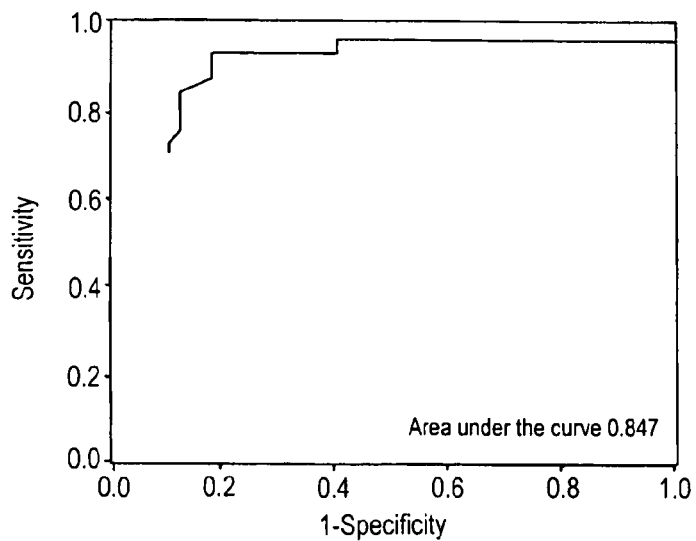

When optimal but equal cut-off (0.12 B) for $RAPD_{DIR}$ and $RAPD_{CONS}$ was used, 90% sensitivity (95% CI=75.7% to 98.1%) and 82% specificity (95% CI=68.6% to 91.4%) were established. FIG. 17 illustrates the receiver operating characteristics (ROC) curve analysis for differentiating normal subjects from glaucoma patients. The area under the curve was 0.91.

However, it is possible to optimise the test examining the range of cut-off values for the direct and consensual data separately. A two dimensional lookup table was constructed in which the direct cut-off (range, 0 to 2 B) was tabulated against the consensual cut-off (range, 0 to 2 B). Table 4 reports the variation in true negative rate as the cut-offs are varied (specificity) using the data of 50 normal subjects. Table 5

TABLE 4

2 × 2 table describing variation in specificity with different cut-off values for $RAPD_{DIR}$ and $RAPD_{CONS}$ Specificity table

| Normal subjects | $RAPD_{CONS}$ | cut-off | cut-off | cut-off | cut-off | cut-off | cut-off | cut-off | cut-off | cut-off | cut-off | cut-off | cut-off | cut-off | cut-off | cut-off | cut-off | cut-off | cut-off | cut-off | cut-off | cut-off |
|---|---|---|---|---|---|---|---|---|---|---|---|---|---|---|---|---|---|---|---|---|---|
| $RAPD_{DIR}$ | 0.82 | 0 | 0.01 | 0.02 | 0.03 | 0.04 | 0.05 | 0.06 | 0.07 | 0.08 | 0.09 | 0.1 | 0.11 | 0.12 | 0.13 | 0.14 | 0.15 | 0.16 | 0.17 | 0.18 | 0.19 | 0.2 |
| cut-off | 0 | 0 | 0.04 | 0.04 | 0.04 | 0.04 | 0.04 | 0.04 | 0.04 | 0.04 | 0.04 | 0.04 | 0.04 | 0.04 | 0.04 | 0.04 | 0.04 | 0.04 | 0.04 | 0.04 | 0.04 | 0.04 |
| cut-off | 0.01 | 0 | 0.48 | 0.5 | 0.5 | 0.5 | 0.52 | 0.52 | 0.54 | 0.54 | 0.54 | 0.56 | 0.6 | 0.6 | 0.6 | 0.6 | 0.6 | 0.6 | 0.6 | 0.6 | 0.6 | 0.6 |
| cut-off | 0.02 | 0 | 0.48 | 0.5 | 0.5 | 0.5 | 0.52 | 0.52 | 0.54 | 0.54 | 0.54 | 0.56 | 0.6 | 0.6 | 0.6 | 0.6 | 0.6 | 0.6 | 0.6 | 0.6 | 0.6 | 0.6 |
| cut-off | 0.03 | 0 | 0.54 | 0.56 | 0.56 | 0.56 | 0.58 | 0.58 | 0.6 | 0.6 | 0.6 | 0.62 | 0.66 | 0.66 | 0.66 | 0.66 | 0.66 | 0.66 | 0.66 | 0.66 | 0.66 | 0.66 |
| cut-off | 0.04 | 0 | 0.54 | 0.56 | 0.56 | 0.56 | 0.58 | 0.58 | 0.6 | 0.6 | 0.6 | 0.62 | 0.66 | 0.66 | 0.66 | 0.66 | 0.66 | 0.66 | 0.66 | 0.66 | 0.66 | 0.66 |
| cut-off | 0.05 | 0 | 0.54 | 0.56 | 0.56 | 0.56 | 0.58 | 0.58 | 0.6 | 0.6 | 0.6 | 0.62 | 0.66 | 0.66 | 0.66 | 0.66 | 0.66 | 0.66 | 0.66 | 0.66 | 0.66 | 0.66 |
| cut-off | 0.06 | 0 | 0.58 | 0.6 | 0.6 | 0.6 | 0.62 | 0.62 | 0.64 | 0.64 | 0.64 | 0.66 | 0.7 | 0.7 | 0.7 | 0.7 | 0.7 | 0.7 | 0.7 | 0.7 | 0.7 | 0.7 |
| cut-off | 0.07 | 0 | 0.64 | 0.68 | 0.68 | 0.68 | 0.7 | 0.7 | 0.72 | 0.72 | 0.72 | 0.74 | 0.78 | 0.78 | 0.78 | 0.78 | 0.78 | 0.78 | 0.78 | 0.78 | 0.78 | 0.78 |
| cut-off | 0.08 | 0 | 0.66 | 0.7 | 0.7 | 0.7 | 0.72 | 0.72 | 0.74 | 0.74 | 0.74 | 0.78 | 0.82 | 0.82 | 0.82 | 0.82 | 0.82 | 0.82 | 0.82 | 0.82 | 0.82 | 0.82 |
| cut-off | 0.09 | 0 | 0.66 | 0.7 | 0.7 | 0.7 | 0.72 | 0.72 | 0.74 | 0.74 | 0.74 | 0.78 | 0.82 | 0.82 | 0.82 | 0.82 | 0.82 | 0.82 | 0.82 | 0.82 | 0.82 | 0.82 |
| cut-off | 0.1 | 0 | 0.66 | 0.7 | 0.7 | 0.7 | 0.72 | 0.72 | 0.74 | 0.74 | 0.74 | 0.78 | 0.82 | 0.82 | 0.82 | 0.82 | 0.82 | 0.82 | 0.82 | 0.82 | 0.82 | 0.82 |
| cut-off | 0.11 | 0 | 0.66 | 0.7 | 0.7 | 0.7 | 0.72 | 0.72 | 0.74 | 0.74 | 0.74 | 0.78 | 0.82 | 0.82 | 0.82 | 0.82 | 0.82 | 0.82 | 0.82 | 0.82 | 0.82 | 0.82 |
| cut-off | 0.12 | 0 | 0.66 | 0.7 | 0.7 | 0.7 | 0.72 | 0.72 | 0.74 | 0.74 | 0.74 | 0.78 | 0.82 | 0.82 | 0.82 | 0.82 | 0.82 | 0.82 | 0.82 | 0.82 | 0.82 | 0.82 |
| cut-off | 0.13 | 0 | 0.66 | 0.7 | 0.7 | 0.7 | 0.72 | 0.72 | 0.74 | 0.74 | 0.74 | 0.78 | 0.82 | 0.82 | 0.82 | 0.82 | 0.82 | 0.82 | 0.82 | 0.82 | 0.82 | 0.82 |
| cut-off | 0.14 | 0 | 0.68 | 0.72 | 0.72 | 0.72 | 0.76 | 0.76 | 0.78 | 0.78 | 0.78 | 0.82 | 0.86 | 0.88 | 0.88 | 0.88 | 0.88 | 0.88 | 0.88 | 0.88 | 0.88 | 0.88 |
| cut-off | 0.15 | 0 | 0.68 | 0.72 | 0.72 | 0.72 | 0.76 | 0.76 | 0.78 | 0.78 | 0.78 | 0.82 | 0.86 | 0.88 | 0.88 | 0.88 | 0.88 | 0.88 | 0.88 | 0.88 | 0.88 | 0.88 |
| cut-off | 0.16 | 0 | 0.68 | 0.72 | 0.72 | 0.72 | 0.76 | 0.76 | 0.78 | 0.78 | 0.78 | 0.82 | 0.86 | 0.88 | 0.88 | 0.88 | 0.88 | 0.88 | 0.88 | 0.88 | 0.88 | 0.88 |
| cut-off | 0.17 | 0 | 0.68 | 0.72 | 0.72 | 0.72 | 0.76 | 0.76 | 0.78 | 0.78 | 0.78 | 0.82 | 0.86 | 0.88 | 0.88 | 0.88 | 0.88 | 0.88 | 0.88 | 0.88 | 0.88 | 0.88 |
| cut-off | 0.18 | 0 | 0.68 | 0.72 | 0.72 | 0.72 | 0.76 | 0.76 | 0.78 | 0.78 | 0.78 | 0.82 | 0.86 | 0.88 | 0.88 | 0.88 | 0.88 | 0.88 | 0.88 | 0.88 | 0.88 | 0.88 |
| cut-off | 0.19 | 0 | 0.68 | 0.72 | 0.72 | 0.72 | 0.76 | 0.76 | 0.78 | 0.78 | 0.78 | 0.82 | 0.86 | 0.88 | 0.88 | 0.88 | 0.88 | 0.88 | 0.88 | 0.88 | 0.88 | 0.88 |
| cut-off | 0.2 | 0 | 0.68 | 0.72 | 0.72 | 0.72 | 0.76 | 0.76 | 0.78 | 0.78 | 0.78 | 0.82 | 0.86 | 0.88 | 0.88 | 0.88 | 0.88 | 0.88 | 0.88 | 0.88 | 0.88 | 0.88 |

TABLE 5

2 × 2 table describing variation in sensitivity with different cut-off values for $RAPD_{DIR}$ and $RAPD_{CONS}$ Sensitivity table

| Glaucoma patients | $RAPD_{CONS}$ | cut-off | cut-off | cut-off | cut-off | cut-off | cut-off | cut-off | cut-off | cut-off | cut-off | cut-off | cut-off | cut-off | cut-off | cut-off | cut-off | cut-off | cut-off | cut-off | cut-off | cut-off |
|---|---|---|---|---|---|---|---|---|---|---|---|---|---|---|---|---|---|---|---|---|---|
| $RAPD_{DIR}$ | 0.806 | 0 | 0.01 | 0.02 | 0.03 | 0.04 | 0.05 | 0.06 | 0.07 | 0.08 | 0.09 | 0.1 | 0.11 | 0.12 | 0.13 | 0.14 | 0.15 | 0.16 | 0.17 | 0.18 | 0.19 | 0.2 |
| cut-off | 0 | 1 | 1 | 0.97 | 0.97 | 0.97 | 0.97 | 0.97 | 0.97 | 0.97 | 0.97 | 0.97 | 0.97 | 0.97 | 0.97 | 0.97 | 0.97 | 0.97 | 0.97 | 0.97 | 0.97 | 0.97 |
| cut-off | 0.01 | 1 | 1 | 0.97 | 0.97 | 0.97 | 0.97 | 0.97 | 0.97 | 0.97 | 0.97 | 0.97 | 0.97 | 0.97 | 0.97 | 0.97 | 0.97 | 0.97 | 0.97 | 0.97 | 0.97 | 0.97 |
| cut-off | 0.02 | 0.97 | 0.97 | 0.94 | 0.94 | 0.94 | 0.94 | 0.94 | 0.94 | 0.94 | 0.94 | 0.94 | 0.94 | 0.94 | 0.94 | 0.94 | 0.94 | 0.94 | 0.94 | 0.94 | 0.94 | 0.94 |
| cut-off | 0.03 | 0.97 | 0.97 | 0.94 | 0.94 | 0.94 | 0.94 | 0.94 | 0.94 | 0.94 | 0.94 | 0.94 | 0.94 | 0.94 | 0.94 | 0.94 | 0.94 | 0.94 | 0.94 | 0.94 | 0.94 | 0.94 |
| cut-off | 0.04 | 0.97 | 0.97 | 0.94 | 0.94 | 0.94 | 0.94 | 0.94 | 0.94 | 0.94 | 0.94 | 0.94 | 0.94 | 0.94 | 0.94 | 0.94 | 0.94 | 0.90 | 0.90 | 0.90 | 0.90 | 0.90 |
| cut-off | 0.05 | 0.97 | 0.97 | 0.94 | 0.94 | 0.94 | 0.94 | 0.94 | 0.94 | 0.94 | 0.94 | 0.94 | 0.94 | 0.94 | 0.94 | 0.94 | 0.94 | 0.90 | 0.90 | 0.90 | 0.90 | 0.90 |
| cut-off | 0.06 | 0.97 | 0.97 | 0.94 | 0.94 | 0.94 | 0.94 | 0.94 | 0.94 | 0.94 | 0.94 | 0.94 | 0.94 | 0.94 | 0.94 | 0.94 | 0.94 | 0.90 | 0.90 | 0.90 | 0.90 | 0.90 |
| cut-off | 0.07 | 0.97 | 0.97 | 0.94 | 0.94 | 0.94 | 0.94 | 0.94 | 0.94 | 0.94 | 0.94 | 0.94 | 0.94 | 0.94 | 0.94 | 0.90 | 0.90 | 0.87 | 0.87 | 0.87 | 0.87 | 0.87 |
| cut-off | 0.08 | 0.97 | 0.97 | 0.94 | 0.94 | 0.94 | 0.94 | 0.94 | 0.94 | 0.94 | 0.94 | 0.94 | 0.94 | 0.94 | 0.94 | 0.90 | 0.90 | 0.87 | 0.87 | 0.84 | 0.84 | 0.84 |
| cut-off | 0.09 | 0.97 | 0.97 | 0.94 | 0.94 | 0.94 | 0.94 | 0.94 | 0.94 | 0.94 | 0.94 | 0.94 | 0.94 | 0.94 | 0.94 | 0.90 | 0.90 | 0.87 | 0.87 | 0.84 | 0.84 | 0.84 |
| cut-off | 0.1 | 0.97 | 0.97 | 0.90 | 0.90 | 0.90 | 0.90 | 0.90 | 0.90 | 0.90 | 0.90 | 0.90 | 0.90 | 0.90 | 0.90 | 0.87 | 0.87 | 0.84 | 0.84 | 0.81 | 0.81 | 0.81 |
| cut-off | 0.11 | 0.97 | 0.97 | 0.90 | 0.90 | 0.90 | 0.90 | 0.90 | 0.90 | 0.90 | 0.90 | 0.90 | 0.90 | 0.90 | 0.90 | 0.87 | 0.87 | 0.84 | 0.84 | 0.81 | 0.81 | 0.81 |
| cut-off | 0.12 | 0.97 | 0.97 | 0.90 | 0.90 | 0.90 | 0.90 | 0.90 | 0.90 | 0.90 | 0.90 | 0.90 | 0.90 | 0.90 | 0.90 | 0.87 | 0.87 | 0.84 | 0.84 | 0.81 | 0.81 | 0.81 |
| cut-off | 0.13 | 0.97 | 0.97 | 0.90 | 0.90 | 0.90 | 0.90 | 0.90 | 0.87 | 0.87 | 0.87 | 0.87 | 0.87 | 0.87 | 0.87 | 0.84 | 0.84 | 0.81 | 0.81 | 0.77 | 0.77 | 0.77 |
| cut-off | 0.14 | 0.97 | 0.97 | 0.90 | 0.90 | 0.87 | 0.87 | 0.87 | 0.84 | 0.84 | 0.84 | 0.84 | 0.84 | 0.84 | 0.84 | 0.81 | 0.81 | 0.77 | 0.77 | 0.74 | 0.74 | 0.74 |
| cut-off | 0.15 | 0.97 | 0.97 | 0.90 | 0.90 | 0.87 | 0.87 | 0.87 | 0.84 | 0.84 | 0.84 | 0.84 | 0.84 | 0.84 | 0.84 | 0.81 | 0.81 | 0.77 | 0.77 | 0.74 | 0.74 | 0.74 |
| cut-off | 0.16 | 0.94 | 0.94 | 0.87 | 0.87 | 0.84 | 0.84 | 0.84 | 0.81 | 0.81 | 0.81 | 0.77 | 0.77 | 0.77 | 0.77 | 0.74 | 0.74 | 0.71 | 0.71 | 0.68 | 0.68 | 0.68 |
| cut-off | 0.17 | 0.94 | 0.94 | 0.87 | 0.87 | 0.84 | 0.84 | 0.84 | 0.81 | 0.81 | 0.81 | 0.77 | 0.77 | 0.77 | 0.77 | 0.74 | 0.74 | 0.71 | 0.71 | 0.68 | 0.68 | 0.68 |
| cut-off | 0.18 | 0.94 | 0.94 | 0.87 | 0.87 | 0.84 | 0.84 | 0.84 | 0.81 | 0.81 | 0.81 | 0.77 | 0.77 | 0.77 | 0.77 | 0.74 | 0.74 | 0.71 | 0.71 | 0.68 | 0.68 | 0.68 |
| cut-off | 0.19 | 0.94 | 0.94 | 0.87 | 0.87 | 0.84 | 0.84 | 0.84 | 0.81 | 0.81 | 0.81 | 0.77 | 0.77 | 0.77 | 0.77 | 0.74 | 0.74 | 0.71 | 0.71 | 0.68 | 0.68 | 0.68 |
| cut-off | 0.2 | 0.94 | 0.94 | 0.87 | 0.87 | 0.84 | 0.84 | 0.84 | 0.81 | 0.81 | 0.81 | 0.77 | 0.77 | 0.77 | 0.77 | 0.74 | 0.74 | 0.71 | 0.71 | 0.68 | 0.68 | 0.68 | reports the variation in true positive rate as the cut-offs are varied (sensitivity) using the data of 33 glaucoma patients. The highlighted areas in table 4 and 5 show the range of cut-offs that can be used for both normal subjects and the glaucoma patients.

Based on different cut-offs for direct and consensual, the optimal cut-offs (maximising both sensitivity and specificity) are 0.08 or 0.09 for direct and 0.11, 0.12 or 0.13 B for consensual, all combinations giving sensitivity of 93.9% (95% CI 79.8% to 99.3%) and specificity of 82% (95% CI 68.6% to 91.4%). Because the $RAPD_{DIR}$ and $RAPD_{CONS}$ have their own cut-offs, essentially the test has been optimised.

We chose the 0.09 B cut-off value for the $RAPD_{DIR}$ and 0.12 B cut-off value for $RAPD_{CONS}$. FIGS. 20(a) and 20(b) describe ROC curve analysis for $RAPD_{DIR}$ and $RAPD_{CONS}$. The area under the curve for $RAPD_{DIR}$ and $RAPD_{CONS}$ were 0.868 and 0.847. When these cut-off values are used, 31 out of 33 glaucoma patients tested negative for RAPD and 41 out of 50 normal subjects tested positive for RAPD.

In the above description, the present invention has been shown to provide an integrated binocular pupillometer which is for assessing relative afferent pupillary defect in a subject and comprises eyepieces for positioning against the eyes of said subject, sensing means adapted to generate and record separate pupillary response data in respect of the left and right eyes, and, commonly housed therewith, left and right stimulating means adapted to apply stimulating visible light pulses independently to said eyes in turn, characterised in that said left and right stimulating means are optically separated by dividing means and each comprise an illuminable screen which has a visible fixation point associated therewith and which is viewable through an object lens positioned between said screen and said eyepiece, said screen and lens being configured such that the observable field of view is at least 9°. It can also be seen that at least in the preferred embodiments, the binocular pupillometer may include any of the following features:

i) the sensing means may comprise means for infrared illumination of each eye to generate images of the pupil and detector means permitting generation of pupillary response data from images so generated;

ii) the screen of each stimulating means may be illuminable by a light-emitting diode positioned outside the field of view;

iii) each said light-emitting diode may generate white light;

iv) each stimulating means may be adapted to apply a sequence of visible light pulse of identical duration, intensity and separation;

v) each left and right stimulating means may be adapted to apply equally spaced alternating visible light pulses to the eyes in turn;

vi) the duration of said pulses may be in the range 0.2-0.5 seconds and the separation between each pulse may be in the range 1-8 seconds;

vii) the pupillometer may be adapted to apply a total of 4-8 pulses to each eye;

viii) the pupillometer may be adapted to apply a total of 7 pulses to each eye, the duration of each pulse being 0.4 seconds and the separation between each alternating pulse being 1.6 seconds;

ix) each visible fixation point may comprise a steadily illuminable coloured light source positioned in contact with or behind an aperture in the corresponding screen;

x) the light of each visible fixation point may be coloured green;

xi) each fixation point and lens may be configured such that the fixation point essentially appears at infinity;

xii) each screen and lens may be configured such that the observable field of view is 10±0.5° or more, e.g., 20+/−2 degrees;

xiii) the pupillary threshold may be determined by variation of the stimulus intensity in a feedback loop;

xiv) the pupillary threshold may be determined by variation of the stimulus duration in a feedback loop;

xv) the pupillary threshold may be determined in the treatment of Leber Congenital Amaurosis;

xvi) the pupillary threshold may be determined in the treatment of Age Related Macular Degeneration;

xvii) the pupillary threshold may be determined in the treatment of retinitis pigmentosa;

xviii) the RAPD may be used to determine the likelihood of primary open angle glaucoma;

xix) the RAPD may be used to measure of the severity of primary open angle glaucoma;

xx) the RAPD may be used to measure the progression of the severity of primary open angle glaucoma;

xxi) the pupillometer may be calibrated to output a value for RAPD in decibels;

xxii) the pupillometer may have a dividing means which reduces the cross-contamination of light to the left and right eyes to less than 1%, more preferably to less than 0.01%;

xxiii) the dividing means may comprise a septum that extends between and divides the left stimulating means from the right stimulating means, the septum further extending between the object lens for the left eye and the object lens for the right eye, and further extending up to and between the left and right eyepieces, thereby defining a left stimulus channel which is isolated optically from a right stimulus channel;

xxiv) the left and right stimulus channels may each comprise a first-surface mirror and a cold mirror located between the object lens and the eyepiece;

xxv) the mirrors of the left and right stimulus channels may not extend through the dividing means;

xxvi) the dividing means may further include a resilient member that extends from the housing of the pupillometer, between the left and right eyepieces, to engage the face of a subject, in order to reduce the cross-contamination of light to the left and right eyes;

xxvii) the resilient member may be of a light-impermeable foam;

xxviii) each visible fixation point comprising a steadily illuminable coloured light source positioned in contact with or behind an aperture in the corresponding screen, may be a green light emitting LED;

xxix) in a method of measuring RAPD, the method may include the steps of measuring the pupil sizes of the left and right eyes without stimulation and determining the amount of reduction in retinal illumination which would result from anisocoria;

xxx) the reduction in retinal illumination may be calculated by determining a value for the square of the smaller pupil diameter divided by the square of the larger pupil diameter;

xxxi) the reduction in retinal illumination may be calculated by determining the negative logarithm of the square of the smaller pupil diameter divided by the square of the larger pupil diameter; and/or xxxii) the calculated reduction in retinal illumination may be taken into account when assessing the RAPD of the subject by:

(i) when there is an apparent RAPD in the eye with the smaller pupil, the RAPD which is attributable to disease is calculated as the apparent RAPD minus the RAPD caused by the anisocoria; and (ii) when there is an apparent RAPD in the eye with the larger pupil, the RAPD which is attributable to disease is calculated as the apparent RAPD plus the RAPD caused by the anisocoria.

The invention claimed is:

1. A binocular pupillometer apparatus for assessing relative afferent pupillary defect in a subject comprising: a binocular pupillometer comprising stimulating means arranged to apply a plurality of stimulating visible light pulses of different intensities independently to each eye and sensing means arranged to generate and record separate pupillary response data in respect of the left and right eyes, the apparatus further including processing means arranged to calculate relative afferent pupillary defect of a subject by:

(i) determining an apparent pupillary response for each of the left and right eyes with respect to intensity from the recorded pupillary response data, wherein the apparent pupillary responses of the left and right eyes are not parallel to each other;

(ii) calculating an area difference D between the apparent pupillary responses of the left and right eyes with respect to intensity;

and then either:

(iii) generating modified pupillary responses for the left and right eyes which are parallel to each other, have a gradient which is intermediate the apparent pupillary responses of the left and right eyes and are separated by the area difference D;

(iv) calculating a value for relative afferent pupillary defect based on the modified pupillary responses of the left and right eyes; and (v) outputting said value for relative afferent pupillary defect which is based on the modified pupillary responses, wherein the processing means is arranged to calculate the gradient of the modified pupillary responses by determining an average of the gradients of the apparent left and right eye pupillary responses, and the processing means is arranged to calculate the area difference D between the apparent pupillary responses by integrating the amplitude of each of the apparent papillary responses with respect to intensity and subtracting one from the other, or;

(iii) calculating an intermediary pupillary response with respect to intensity which is intermediate the apparent pupillary responses of the left and right eyes and determining a modified pupillary response for the left or right eye with respect to intensity which follows the intermediary pupillary response and is separated from the modified pupillary response of the left or right eye by an area difference D/2;

(iv) calculating a value for relative afferent pupillary defect based on the intermediary pupillary response and the modified pupillary response of the left or right eye; and (v) outputting said value for the relative afferent pupillary defect which is based on the intermediary and the modified pupillary response, wherein the processing means is arranged to calculate the gradient of the intermediary pupillary response and the modified pupillary response by determining an average of the gradients of the apparent left and right eye pupillary responses, and the processing means is arranged to calculate the area difference D between the apparent pupillary responses by integrating the amplitude of each of the apparent pupillary responses with respect to intensity and subtracting one from the other.

2. The apparatus of claim 1, wherein the processing means is housed within the binocular pupillometer.

3. The apparatus of claim 1, wherein the processing means is arranged to calculate the area difference D over an intensity range of 20 dB.

4. The apparatus of claim 1, wherein the processing means is arranged to calculate the value for the relative afferent pupillary defect by determining the separation along the intensity axis of the modified pupillary responses for the left and right eyes at a given amplitude of pupillary constriction.

5. The apparatus of claim 1, wherein the binocular pupillometer is an integrated binocular pupillometer comprising eyepieces for positioning against the eyes of said subject, sensing means adapted to generate and record separate pupillary response data in respect of the left and right eyes, and, commonly housed therewith, left and right stimulating means adapted to apply stimulating visible light pulses independently to said eyes in turn, wherein said left and right stimulating means are optically separated by dividing means and each comprise an illuminable screen which has a visible fixation point associated therewith and which is viewable through an object lens positioned between said screen and said eyepiece, said screen and lens being configured such that the observable field of view is at least 9°.

6. A method of assessing relative afferent pupillary defect in a subject from pupillary response data of the constriction observed in each of lett and right eyes when stimulated independently with visible light pulses at different light intensities, wherein the method comprises:

(i) determining an apparent pupillary response for each of left and right eyes with respect to intensity from recorded pupillary response data, wherein the apparent pupillary responses of the left and right eyes are not parallel to each other;

(ii) calculating an area difference D between the apparent pupillary responses of the left and right eyes with respect to intensity;

and then either:

(iii) generating modified pupillary responses for the left and right eyes which are parallel to each other, have a gradient which is intermediate the apparent pupillary responses of the left and right eyes and are separated by the area difference D;

(iv) calculating a value for relative afferent pupillary detect based on the modified pupillary responses of the left and right eyes; and (v) outputting said value for relative afferent pupillary defect which is based on the modified pupillary responses, wherein the gradients of the modified pupillary responses are an average of the apparent left and right eye pupillary responses and the area difference D between the apparent pupillary responses is calculated by integrating the amplitude of each of the apparent pupillary responses with respect to intensity and subtracting one from the other, or:

(iii) calculating an intermediary pupillary response with respect to intensity which is intermediate the apparent pupillary responses of the left and right eyes and determining a modified pupillary response for the left or right eye with respect to intensity which follows the intermediary pupillary response and is separated from the modified pupillary response of the left or right eye by an area difference D/2, (iv) calculating a value for relative afferent pupillary defect based on the intermediary pupillary response and the modified pupillary response of the left or right eye; and (v) outputting said value for relative afferent pupillary defect which is based on the intermediary pupillary response and the modified pupillary response, wherein the gradient of the intermediary pupillary response and the modified pupillary response is an average of the apparent left and right eye pupillary responses and the area difference D between the apparent pupillary responses is calculated by intgraging the amplitude of each of the apparent pupillary responses with respect to intensity and subtracting one from the other.

7. The method of claim 6, wherein the step of outputting said value for relative afferent pupillary defect (RAPD) includes: outputting a value for RAPD based on apparent pupillary responses which are measured for each eye under direct stimulation conditions; and outputting a value for RAPD based on apparent pupillary responses which are measured for each eye under consensual stimulation conditions.

8. The method of claim 6, wherein the area difference D is calculated over an intensity range of 20 dB.

9. The method of claim 6, wherein the value for the relative afferent pupillary defect is calculated by determining the separation along the intensity axis of the modified pupillary responses for the left and right eyes at a given amplitude of pupillary constriction.

* * * * *